United States Patent [19]

Thomas et al.

[11] Patent Number: 5,604,201
[45] Date of Patent: Feb. 18, 1997

[54] METHODS AND REAGENTS FOR INHIBITING FURIN ENDOPROTEASE

[75] Inventors: Gary Thomas, Tualatin; Eric D. Anderson, Portland; Laurel Thomas, Tualatin, all of Oreg.; Joel S. Hayflick, Seattle, Wash.

[73] Assignee: State of Oregon, Acting by and through the Oregon State Board of Higher Education on Behalf of the Oregon Health Sciences University, a non-profit organization, Portland, Oreg.

[21] Appl. No.: 2,202

[22] Filed: Jan. 8, 1993

[51] Int. Cl.$^6$ ............... C07K 14/81; C07H 21/04; A61K 38/55; C12N 1/21; C12N 1/15; C12N 15/63
[52] U.S. Cl. ............... 514/12; 530/350; 536/23.5; 435/254.2; 435/320.1; 435/252.3
[58] Field of Search ............... 530/350; 536/23.2, 536/23.5; 435/252.3, 320.1; 514/12

[56] References Cited

U.S. PATENT DOCUMENTS

| | | | |
|---|---|---|---|
| 4,732,973 | 3/1985 | Barr et al. | 530/350 |
| 5,460,950 | 10/1995 | Barr et al. | 435/69.1 |

OTHER PUBLICATIONS

Berger & Shooter, "Evidence for pro–β–nerve growth factor, a biosynthetic precursor to β–nerve growth factor", 1977, Proc. Natl. Acad. Sci. USA 74: 3647–3651.
Knowles et al., "Human hepatocellular carcinoma cell lines secrete the major plasma proteins and hepatitis B surface antigen", 1980, Science 209: 497–499.
Scheller et al., "A single gene encodes multiple neuropeptides mediating a stereotyped behavior", 1983, Cell 32: 7–22.
Gray et al., "Nucleotide sequence of epidermal growth factor cDNA predicts a 128,000–molecular weight protein precursor", 1983, Nature 303: 722–725.
Morrison et al., "Intracellular processing of the Newcastle Disease virus fusion glycoprotein", 1985, J. Virol. 53: 851–857.
Rice et al., "Nucleotide sequence of yellow fever virus: Implications for flavivirus gene expression and evolution", 1985, Science 229: 726–733.
Bentley et al., "Defective propeptide processing of blood clotting Factor IX caused by mutation of arginine to glutamine at position –4", 1986, Cell 45: 343–348.
Bonthron et al., "Structure of pre–pro–von Willebrand factor and its expression in heterologous cells", 1986, Nature 324: 270–273.
Keller et al., "Identification and structure of the gene encoding gpII, a major glycoprotein of varicella–zooster virus", 1986, Virology 152: 181–191.

Richardson et al., "The nucleotide sequence of the mRNA encoding the fusion protein of measles virus (Edmonston strain): A comparison of fusion proteins from several different paramyxoviruses", 1986, Virology 155: 508–523.
Perez & Hunter, "Mutations within the proteolytic cleavage site of the Rous sarcoma virus glycoprotein that block processing to gp85 and gp37", 1987, J. Virol. 61: 1609–1614.
Waxham et al., "Cloning and sequencing of the mumps virus fusion protein", 1987, Virology 159: 381–389.
McCune et al., "Endoproteolytic cleavage of gp160 is required for the activation of Human immunodeficiency virus", 1988, Cell 53: 55–67.
Gentry et al., "Molecular events in the processing of recombinant type 1 pre–pro–transforming growth factor β to the mature polypeptide", 1988, Molec. Cell. Biol. 8: 4162–4168.
Edwards et al., "Processing and secretion of nerve growth factor: Expression in mammalian cells with a vaccinia virus vector", 1988, Molec. Cell Biol. 8: 2456–2464.
Yamada et al., "Intracellular processing of mumps virus glycoproteins", 1988, Virology 165: 268–273.
Fuller et al., "Enzymes required for yeast prohormone processing", 1988, Ann. Rev. Physiol. 50: 345–362.
Yoshimasa et al., "Insulin–resistant diabetes due to a point mutation that prevents insulin proreceptor processing", 1988, Science 240: 784–787.
Ciepak et al., "Specific cleavage of diphtheria toxin by human urokinase", 1988, Biochem. Biophys. Res. Comm. 157: 747–754.

(List continued on next page.)

*Primary Examiner*—Robert A. Wax
*Assistant Examiner*—Kawai Lau
*Attorney, Agent, or Firm*—Banner & Allegretti, Ltd.

[57] ABSTRACT

This invention relates to methods and reagents for inhibiting furin endoprotease activity and specifically for inhibiting furin endoprotease-mediated maturation of bioactive proteins in vivo and in vitro. The invention specifically provides proteins capable of inhibiting furin endoprotease activity. Particularly provided are $\alpha_1$-antitrypsin variants that specifically inhibit furin endoprotease activity. Methods for using furin endoprotease inhibition to attenuate or prevent viral protein maturation, and thereby alleviate viral infections, are provided. Also provided are methods for using furin endoprotease inhibition to attenuate or prevent proteolytic processing of bacterial toxins, thereby alleviating bacterial infections. Methods are also provided to inhibit proteolytic processing of biologically active proteins and peptides. The invention also provides pharmaceutically acceptable compositions of therapeutically effective amounts of furin endoprotease inhibitors.

14 Claims, 6 Drawing Sheets

OTHER PUBLICATIONS

Sossin et al., "Cellular and molecular biology of neuropeptide processing and packaging", 1989, Neuron 2: 1407–1417.

Singh et al., "Internalization and processing of *Bacillus anthacis* lethal toxin by toxin-sensitive and -resistant cells", 1989, J. Biol. Chem. 264: 11099–11102.

Garten et al., "Inhibition of proteolytic activation of influenza virus hemagglutinin by specific peptidyl chloroalkyl ketones", 1989, Virology 172: 25–31.

Randolph et al., "Acidotropic amines inhibit proteolytic processing of flavivirus prM protein", 1990, Virology 174: 450–458.

Spaete et al., "Sequence requirements for proteolytic processing of glycoprotein B of human cytomegalovirus straine Towne", 1990, J. Virol. 64: 2922–2931.

Ogata et al., "Processing of Pseudomonas exotoxin by a cellular protease results in the generation of a 37,000-Da toxin fragment that is translocated to the cytosol", 1990, J. Biol. Chem. 265: 20678–20685.

Wise et al., "Expression of a human proprotein processing enzyme: Correct cleavage of the von Willebrand factor precursor at a paired basic amino acid site", 1990, Proc. Natl. Acad. Sci. USA 87: 9378–9382.

Barr, "Mammalian subtilisins: The long-sought dibasic processing endoproteases", 1991, Cell 66: 1–3.

Hosaka et al., "Arg–X–Lys/Arg–Arg motif as a signal for precursor cleavage catalyzed by furin within a constitutive secretory pathway", 1991, J. Biol. Chem. 266: 12127–12130.

Klimpel et al., "Anthrax toxin protective antigen is activated by a cell surface protease with the sequence specificity and catalytic properties of furin", 1992, Proc. Natl. Acad. Sci. USA 89: 10277–10281.

Bresnahan et al., "Human fur gene encodes a yeast KEX2-like endoprotease that cleaves pro–β–NGF in vivo", 1990, J. Cell Biol. 111: 2851–2859.

Molloy et al., "Human furin is a calcium–dependent serine endoprotease that recognizes the sequence Arg–X–X–Arg and efficiently cleaves anthrax toxin protective antigen", 1992, J. Biol. Chem. 267: 16396–16402.

Steineke–Grober et al., "Influenza virus hemagglutinin with a multibasic cleavage site is activated by furin, a subtilisin–like endoprotease", 1992, EMBO J. 11: 2407–2414.

van den Ouweland et al., "Hemagglutinin activation of pathogenic avian influenza viruses of serotype H7 requires the protease recognition motif R–X–K/R–R", 1992, Nucleic Acids Res. 18: 664.

Klimpel et al., 1992, Annual Meeting, Amer. Soc. Microbiol. Abst. B–32.

Vey et al., "Structural homology between the human *fur* gene product and the subtilisin–like protease encoded by yeast KEX2", 1992, Virology 188: 408–413.

Oda et al. (1992) "Proteolytic Cleavages of Proalbumin . . . " *Biochem. Biophys. Res. Comm.* 189 (3):1353–1361.

George et al. (1989) "Characterization of antithrombins produced . . . " *Blood* 73(2):490–496.

METHODS AND REAGENTS FOR INHIBITING FURIN ENDOPROTEASE

This invention was made with government support under DK44629 and DK37274 from the National Institutes of Health. The government has certain rights in the invention.

BACKGROUND OF THE INVENTION

1. Field of the Invention

This invention relates to endoproteases, particularly a novel endoprotease termed furin endoprotease. The invention also relates to inhibitors of furin endoprotease activity. In particular, the invention relates to novel variants of $\alpha_1$-antitrypsin that specifically inhibit furin endoprotease activity. The invention also provides methods for using such inhibitors to attenuate or prevent biological proteolytic maturation of bioactive proteins and peptides in vivo and in vitro, in particular viral proteins and bacterial toxins. Therapeutic methods and pharmaceutical compositions of such inhibitors are also provided directed towards the alleviation and treatment of disease having microbiological etiology.

2. Information Disclosure Statement

Most biologically active peptides and proteins are synthesized initially as larger, inactive precursor proteins that are endoproteolytically cleaved during transit through the secretory pathway in the Golgi apparatus in cells expressing such proteins (see Barr, 1991, Cell 66: 1–3 for review). This system comprises an important common mechanism required for synthesis of biologically active proteins and peptides in yeast (Fuller et al., 1988, Ann. Rev. Physiol. 50: 345–362), invertebrates (Scheller et al., 1983, Cell 32: 7–22) and mammalian cells (Sossin et al., 1989, Neuron 2: 1407–1417). Examples of proteins produced in vivo by exocytotic transport through the Golgi are precursors of peptide hormones, neuropeptides, growth factors, coagulation factors, serum albumin, cell surface receptors, and adhesion molecules.

Morrison et al., 1985, J. Virol. 53: 851–857 disclose that F protein of Newcastle disease virus is processed through the exocytotic transport pathway in infected cells.

Perez & Hunter, 1987, J. Virol. 61: 1609–1614 disclose that the Rous sarcoma virus (RSV) glycoprotein is processed through the exocytotic transport pathway in infected cells.

Yamada et al., 1988, Virology 165: 268–273 disclose that F protein of mumps virus is processed through the exocytotic transport pathway in infected cells.

Randolph et al., 1990, Virology 174: 450–458 disclose that the prM protein of flaviviruses is processed through the exocytotic transport pathway in infected cells.

A common structural feature of molecules processed through the exocytotic transport pathway is the presence of basic residues or pairs of basic residues at the proteolytic processing site in the molecule. Examples include serum factors (Factor IX; Bentley et al., 1986, Cell 45: 343–348; proalbumin; Knowles et al., 1980, Science 209: 497–499; pro-von Willibrand factor; Bonthron et al., 1986, Nature 324: 270–273), viral polyproteins (human immunodeficiency virus (HIV) gp160; McCune et al., 1988, Cell 53: 55–67; RSV envelope protein; Perez & Hunter, 1987, J. Virol. 61: 1609–1614; yellow fever virus protein; Rice et al., 1985, Science 229: 726–733; measles virus protein; Richardson et at., 1986, Virology 155: 508–523; mumps virus protein; Waxham et al., 1987, Virology 159: 381–389; human cytomegalovirus protein; Spaete et al., 1990, J. Virol. 64: 2922–2931; varicella zoster virus protein; Keller et al., 1986, Virology 152: 181–191), growth factors (pre-protransforming growth factor $\beta$; Gentry et al., 1988, Molec. Cell. Biol. 8: 4162–4168; epidermal growth factor; Gray et al., 1983, Nature 303: 722–725; pro-$\beta$-nerve growth factor (NGF); Edwards et al., 1988, Molec. Cell Biol. 8: 2456–2464), receptors (insulin receptor; Yoshimasa et al., 1988, Science 240: 784–787); and bacterial toxins (see Stephen & Pietrowski, 1986, *Bacterial Toxins*, 2d ed. (Amer. Soc. Microbiol. Washington, D.C.) for review; anthrax toxin; Singh et at., 1989, J. Biol. Chem. 264: 11099–11102). The proteolytic processing site has been identified in some of these molecules.

Berger & Shooter, 1977, Proc. Natl. Acad. Sci. USA 74:3647–3651 disclose the sequence -RSKR- (SEQ ID No.:1) at the proteolytic processing site of pro-$\beta$-NGF.

Bentley et al., 1986, ibid. disclose the sequence -RPKR- (SEQ ID No.:2) at the proteolytic processing site of the blood coagulation factor protein Factor IX.

McCune et al., 1988, ibid., disclose the sequence -REKR- (SEQ ID No.:3) at the proteolytic processing site of HIV gp160.

Ciepak et al., 1988, Biochem. Biophys. Res. Comm. 157:747–754 disclose the sequence -RVRR- (SEQ ID No.:4) at the proteolytic processing site of diphtheria toxin.

Vey et al., 1992, Virology 188: 408–413 disclose the sequence -RX(R/K)R- (SEQ ID No.:5) at the proteolytic processing site of influenza hemagglutinin.

Ogata et al., 1990, J. Biol. Chem. 265: 20678–20685 disclose the sequence -RSKR- (SEQ ID No.:1) at the proteolytic processing site of Pseudomonas exotoxin A.

Klimpel et al., 1992, Proc. Natl. Acad. Sci. USA 89: 10277–10281 disclose the sequence -RX(R/K)R- (SEQ ID No.:5) at the proteolytic processing site of anthrax protective antigen.

Recently, an endoprotease termed furin has been isolated that specifically recognizes the recognition sequence of proteins processed through the exocytotic secretory pathway (Wise et al., 1990, Proc. Natl. Acad. Sci. USA 87: 9378–9382; Bresnahan et al., 1990, J. Cell Biol. 111: 2851–2859). This endoprotease is a subtilisin related, calcium-dependent serine protease (Bresnahan et al., ibid.). A complementary DNA copy of the mRNA encoding this endoprotease has been isolated (Wise et al., ibid.) and sequenced (van den Ouweland et al., 1992, Nucleic Acids Res. 18: 664) and expressed in heterologous cells (Bresnahan et al., ibid.). These studies have shown furin to be expressed as a doublet of 96 and 90 kilodaltons (kD) in size, ubiquitously expressed as a 4.5 kilobase (kb) mRNA, and localized by fluorescence immunohistochemistry to the Golgi apparatus of cells expressing this endoprotease (Bresnahan et al., ibid.). Furin has been shown to be capable of proteolytically cleaving a number of exocytotically processed proteins.

Bresnahan et al., ibid., disclose furin-mediated cleavage of pro-$\beta$-NGF.

Wise et al., ibid., disclose furin-mediated cleavage of pro-von Willibrand factor and complement factor C3.

Hosaka et al., 1991, J. Biol. Chem. 266: 12127–12130 disclose furin-mediated cleavage of renin.

Steineke-Grober et al., 1992, EMBO J. 11: 2407–2414 disclose furin-mediated cleavage of influenza hemagglutinin.

Klimpel et al., 1992, Proc. Natl. Acad. Sci. USA 89: 10277–10281 disclose furin-mediated cleavage of anthrax protective antigen.

Molloy et al., 1992, J. Biol. Chem 267: 16396–16402 disclose furin-mediated cleavage of anthrax protective antigen.

Klimpel et al., 1992, Annual Meeting, Amer. Sco. Microbiol. Abst. B-32 disclose furin-mediated cleavage of diphtheria toxin.

Furin can be inhibited by specific peptidyl chloroalkylketones (Garten et al., 1989, Virology 172: 25–31; Molloy et al., 1992 J Biol. Chem., 267:6396–16402), but these substances are toxic in vivo. Given the importance of this endoprotease in activation of bacterial toxins, viral structural proteins and bioactive molecules, there is a need for the development of safe and specific furin inhibitors.

SUMMARY OF THE INVENTION

This invention provides safe, specific and effective inhibitors of furin endoprotease that are novel variants of the naturally-occuring protease inhibitor, $\alpha_1$-antitrypsin. Use of these novel variants of $\alpha_1$-antitrypsin is advantageous because $\alpha_1$-antitrypsin (SEQ ID No.:6) and variants are secreted proteins that are processed by the exocytotic secretory pathway through the Golgi, so synthesis of these proteins in a cell would result in delivery of the inhibitor to the site of furin activity in vivo.

In a first embodiment, the invention provides a furin endoprotease inhibitor comprising an $\alpha_1$-antitrypsin variant having an amino acid sequence comprising the amino acids of the native $\alpha_1$-antitrypsin molecule, except that the sequence at position 355–358 of the native protein (-Ala-Ile-Pro-Met-) (SEQ ID No.:7) is changed to the novel sequence -Arg-X-X-Arg-, (SEQ ID No.:8) wherein X is any amino acid, at positions 355–358 of the native $\alpha_1$-antitrypsin amino acid sequence. In a preferred embodiment, the $\alpha_1$-antitrypsin variant is $\alpha_1$-antitrypsin Portland (SEQ ID No.:9) and the amino acid sequence at positions 355–358 of the $\alpha_1$-antitrypsin amino acid Portland sequence is -Arg-Ile-Pro-Arg- (SEQ ID No.:10).

In a second embodiment, the invention provides a nucleic acid having a nucleotide sequence that encodes an $\alpha_1$-antitrypsin variant encoding protein having an amino acid sequence comprising the amino acids of the native $\alpha_1$-antitrypsin molecule, except that the sequence at position 355–358 of the native protein (-Ala-Ile-Pro-Met-) (SEQ ID No.:7) is changed to the novel sequence -Arg-X-X-Arg- (SEQ ID No.:8), wherein X is any amino acid, at positions 355–358 of the native $\alpha_1$-antitrypsin amino acid sequence. In a preferred embodiment, the $\alpha_1$-antitrypsin variant is $\alpha_1$-antitrypsin Portland and the amino acid sequence is -Arg-Ile-Pro-Arg- (SEQ ID No.:10).

In a third embodiment, the invention provides a recombinant expression construct comprising a nucleic acid having a nucleotide sequence encoding an $\alpha_1$-antitrypsin protein with an amino acid sequence comprising the amino acids of the native $\alpha_1$-antitrypsin molecule, except that the sequence at position 355–358 of the native protein (-Ala-Ile-Pro-Met-) (SEQ ID No.:7) is changed to the novel sequence -Arg-X-X-Arg- (SEQ ID No.:8), wherein X is any amino acid, at positions 355–358 of the native $\alpha_1$-antitrypsin amino acid sequence. In a preferred embodiment, the $\alpha_1$-antitrypsin variant is $\alpha_1$-antitrypsin Portland and the amino acid sequence is -Arg-Ile-Pro-Arg- (SEQ ID No.:10). The recombinant expression construct provided by the invention is capable of expressing $\alpha_1$-antitrypsin variants of the invention in a culture of transformed cells. In a preferred embodiment, the recombinant expression construct comprises a vaccinia virus-based construct. In a more preferred embodiment, the recombinant expression construct comprises a recombinant vaccinia virus vector covalently linked to the nucleic acid encoding the $\alpha_1$-antitrypsin variant, preferably $\alpha_1$-antitrypsin Portland.

The invention also provides a cell culture transformed with the recombinant expression construct encoding an $\alpha_1$-antitrypsin variant capable of expressing the $\alpha_1$-antitrypsin variant. In a preferred embodiment, the $\alpha_1$-antitrypsin variant is $\alpha_1$-antitrypsin Portland. Preferred embodiments of such cell cultures are cultures of bacterial cells, yeast cells, insect cells or mammalian cells.

In another embodiment, the invention provides a homogenous composition of matter comprising an $\alpha_1$-antitrypsin variant produced by the cell culture according to the teachings of the invention. In a preferred embodiment, the $\alpha_1$-antitrypsin variant is $\alpha_1$-antitrypsin Portland.

The invention also provides a furin endoprotease inhibitor comprising $\alpha_1$-antitrypsin variants capable of blocking endoproteolytic activation of bacterial toxins. In a preferred embodiment, the $\alpha_1$-antitrypsin variant is $\alpha_1$-antitrypsin Portland. Pharmaceutically acceptable compositions of the $\alpha_1$-antitrypsin variants of the invention are also provided comprising a therapeutically effective amount of $\alpha_1$-antitrypsin variant and a pharmaceutically acceptable carrier or diluent.

The invention provides a method of inhibiting bacterial infection of human cells comprising contacting such cells with an $\alpha_1$-antitrypsin variant of the invention. In a preferred embodiment, the $\alpha_1$-antitrypsin variant is $\alpha_1$-antitrypsin Portland. In a preferred embodiment, the bacterial infection is caused by *Corynebacterium diptheriae*. In another preferred embodiment, the bacterial infection is caused by *Bacillus anthracis*.

The invention also provides a method of inhibiting bacterial infection in a human comprising administering a therapeutically effective amount of an $\alpha_1$-antitrypsin variant of the invention in a pharmaceutically acceptable carrier. In a preferred embodiment, the $\alpha_1$-antitrypsin variant is $\alpha_1$-antitrypsin Portland. In a preferred embodiment, the bacterial infection is caused by *Corynebacterium diptheriae*. In another preferred embodiment, the bacterial infection is caused by *Bacillus anthracis*.

The invention provides a method of treating humans with a bacterial infection comprising administering a therapeutically effective amount of an $\alpha_1$-antitrypsin variant of the invention in a pharmaceutically acceptable carrier. In a preferred embodiment, the $\alpha_1$-antitrypsin variant is $\alpha_1$-antitrypsin Portland. In a preferred embodiment, the bacterial infection is caused by *Corynebacterium diptheriae*. In another preferred embodiment, the bacterial infection is caused by *Bacillus anthracis*.

Another method provided by the invention for treating humans with a bacterial infection comprises administering a combination of a therapeutically effective amount of an $\alpha_1$-antitrypsin variant and a therapeutically effective mount of a second antibacterial compound in a pharmaceutically acceptable carrier. In a preferred embodiment, the $\alpha_1$-antitrypsin variant is $\alpha_1$-antitrypsin Portland. In a preferred embodiment, the bacterial infection is caused by *Corynebacterium diptheriae*. In another preferred embodiment, the bacterial infection is caused by *Bacillus anthracis*.

Pharmaceutically acceptable compositions effective according to the methods of the invention, comprising a therapeutically effective amount of a furin endoprotease inhibitor capable of blocking endoproteolytic activation of bacterial toxins and a pharmaceutically acceptable carrier or diluent, are also provided.

The invention provides a method of inhibiting viral infection of human cells comprising contacting such cells with an $\alpha_1$-antitrypsin variant according to the invention. In a preferred embodiment, the invention provides a gene therapy delivery system for a nucleic acid encoding an $\alpha_1$-antitrypsin variant comprising the recombinant expression construct of the invention and genetic means for delivery and expression of the recombinant expression construct into the cells of an animal. A preferred $\alpha_1$-antitrypsin variant is $\alpha_1$-antitrypsin Portland. Pharmaceutically acceptable compositions comprising a therapeutically effective amount of the gene therapy delivery system and a pharmaceutically acceptable carrier or diluent. In a preferred embodiment, the viral infection is caused by Human Immunodeficiency Virus 1 (HIV-1). In another preferred embodiment, the human cells are hematopoietic cells, most preferably T lymphocytes. Other preferred embodiments of viral infections include infection by influenza virus.

The invention also provides a method for inhibiting viral infection in an animal, most preferably a human, comprising administering a therapeutically effective amount of the gene therapy delivery system of the invention in a pharmaceutically acceptable carrier. In a preferred embodiment, the virus is Human Immunodeficiency Virus 1 (HIV-1). In another preferred embodiment, the virus is influenza virus.

The invention provides a method of treating humans infected with a virus comprising administering a therapeutically effective amount of the gene therapy delivery system of the invention in a pharmaceutically acceptable carrier. In a preferred embodiment, the virus is Human Immunodeficiency Virus 1 (HIV-1). In another preferred embodiment, the virus is influenza virus.

The invention provides a method of treating humans infected with a virus comprising administering a combination of a therapeutically effective amount of the gene therapy delivery system of the invention and a therapeutically effective amount of a second antiviral compound in a pharmaceutically acceptable carrier. In a preferred embodiment, the virus is Human Immunodeficiency Virus 1 (HIV-1) and the second antiviral compound is azidothymidine. In another preferred embodiment, the virus is influenza virus.

The invention also provides a method for treating virus-associated immunosuppression in a human comprising administering a therapeutically effective amount of the gene therapy delivery system of the invention in a pharmaceutically acceptable carrier. In a preferred embodiment, the virus is Human Immunodeficiency Virus 1 (HIV-1).

Pharmaceutically acceptable compositions effective according to the methods of the invention, comprising a therapeutically effective amount of the gene therapy delivery system encoding $\alpha_1$-antitrypsin variants having antiviral properties and a pharmaceutically acceptable carrier or diluent, are also provided. In a preferred embodiment, the $\alpha_1$-antitrypsin variant is $\alpha_1$-antitrypsin Portland The invention also provides a method of inhibiting proteolytic processing of a biologically active protein or peptide in a cell comprising contacting such cells with the gene therapy delivery system of the invention. Preferred biologically active proteins are pro-β-nerve growth factor, blood coagulation factor protein Factor IX, pro-von Willibrand factor, complement factor C3 and renin.

Figure 1:
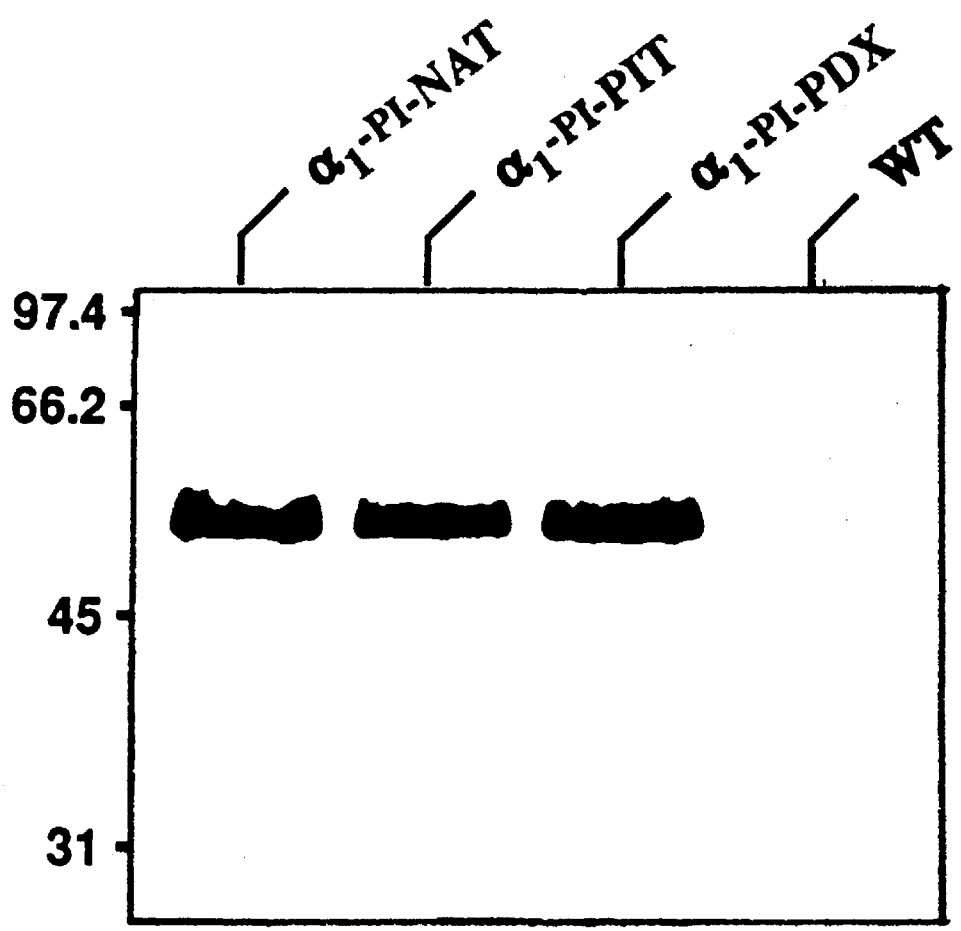
FIG. 1 illustrates production of native $\alpha_1$-antitrypsin (Lane 1), $\alpha_1$-antitrypsin Pittsburgh (Lane 2) and $\alpha_1$-antitrypsin Portland (Lane 3) by BSC-40 cells infected with vaccinia virus recombinant constructs.

FIG. 5 illustrates the experimental protocol for assaying the gp41-mediated fusogenic capacity of gp160-producing IP/IR cells to form syncytia with $CD4^+$ human HeLa cells in the presence and absence of co-expressed $\alpha_1$-antitrypsin and variants.

FIG. 6 illustrates the results of the syncytium experiments described in Example 5.

DETAILED DESCRIPTION OF THE PREFERRED EMBODIMENTS

The production of proteins such as the $\alpha_1$-antitrypsin Portland from cloned genes by genetic engineering is well known. See, e.g., U.S. Pat. No. 4,761,371 to Bell et al. at Col. 6 line 3 to Col. 9 line 65. (The disclosure of all U.S. patent references cited herein is to be incorporated herein by reference.) The discussion which follows is accordingly intended as an overview of this field, and is not intended to reflect the full state of the art. For the purposes of this discussion, the $\alpha_1$-antitrypsin variant $\alpha_1$-antitrypsin Portland will be used as an exemplar; it will be understood that the discussion applies to and the invention encompasses all the $\alpha_1$-antitrypsin variants of the invention.

DNA which encodes $\alpha_1$-antitrypsin Portland may be obtained, in view of the instant disclosure, by chemical synthesis, or by in vitro mutagenesis as described in Example 2 herein of the native $\alpha_1$-antitrypsin DNA sequence. Such native $\alpha_1$-antitrypsin DNA can be obtained by screening reverse transcripts of mRNA from appropriate cells or cultured cell lines, by screening genomic libraries from appropriate cells, or by combinations of these procedures. Screening of mRNA or genomic DNA may be carried out with probes generated from the known $\alpha_1$-antitrypsin gene sequence. Probes may be labeled with a detectable group such as a fluorescent group, a radioactive atom or a chemiluminescent group in accordance with known procedures and used in conventional hybridization assays (see Sambrook et al., 1990, *Molecular Cloning: A Laboratory Manual,* Cold Spring Harbor Laboratory Press, N.Y.). In the alternative, $\alpha_1$-antitrypsin gene sequences may be obtained for in vitro mutagenesis by use of the polymerase chain reaction (PCR) procedure, with the PCR oligonucleotide primers being produced from the native $\alpha_1$-antitrypsin gene sequence. See U.S. Pat. Nos. 4,683,195 to Mullis et al. and 4,683,202 to Mullis.

$\alpha_1$-antitrypsin variants such as $\alpha_1$-antitrypsin Portland may be synthesized in host cells transformed with a recombinant expression construct comprising a DNA sequence encoding an $\alpha_1$-antitrypsin variant. Such a recombinant expression construct can also be comprised of a vector that is a replicable DNA construct. Vectors are used herein either to amplify DNA encoding $\alpha_1$-antitrypsin Portland and/or to express DNA encoding $\alpha_1$-antitrypsin Portland. For the purposes of this invention, a recombinant expression construct is a replicable DNA construct in which a DNA sequence encoding an $\alpha_1$-antitrypsin variant is operably linked to suitable control sequences capable of effecting the expression of the $\alpha_1$-antitrypsin variant in a suitable host. The need for such control sequences will vary depending upon the host selected and the transformation method chosen. Generally, control sequences include a transcriptional promoter, an optional operator sequence to control transcription, a sequence encoding suitable mRNA ribosomal binding sites, and sequences which control the termination of transcription and translation. Amplification vectors do not require expression control domains. All that is needed is the ability to replicate in a host, usually conferred by an origin of replication, and a selection gene to facilitate recognition of transformants.

DNA regions are operably linked when they are functionally related to each other. For example: a promoter is operably linked to a coding sequence if it controls the transcription of the sequence; a ribosome binding site is operably linked to a coding sequence if it is positioned so as to permit translation. Generally, operably linked means contiguous and, in the case of leaders sequences, contiguous and in the same translational reading frame.

Vectors useful for practicing the present invention include plasmids, viruses (including phage), retroviruses, and integratable DNA fragments (i.e., fragments integratable into the host genome by homologous recombination). The vector may replicate and function independently of the host genome, or may, in some instances, integrate into the genome itself. Suitable vectors will contain replicon and control sequences which are derived from species compatible with the intended expression host. A preferred vector is the plasmid pVZneo, useful for producing recombinant expression constructs based on homologous recombination with vaccinia virus sequences.

A preferred embodiment of the recombinant expression constructs of this invention comprise vaccinia virus sequences capable of infecting mammalian cells and expressing $\alpha_1$-antitrypsin variant, as described below in Example 2.

Transformed host cells are cells which have been transformed or transfected with a recombinant expression construct made using recombinant DNA techniques and comprising sequences encoding an $\alpha_1$-antitrypsin variant. Transformed host cells may express $\alpha_1$-antitrypsin Portland, but host cells transformed for purposes of cloning or amplifying DNA need not express these sequences.

Cultures of cells, including cells derived from multicellular organisms, are a desirable hosts for recombinant $\alpha_1$-antitrypsin Portland synthesis. In principal, any cell culture is useful that is capable of being transformed with an appropriate recombinant expression construct and expressing $\alpha_1$-antitrypsin protein. The invention is preferably practiced with bacterial, yeast, insect or mammalian cells, however, mammalian cells are more preferred, as illustrated in the Examples. Propagation of bacteria and yeast is well known in the art, and propagation of mammalian cells in cell culture has become a routine procedure. See *Tissue Culture*, Academic Press, Kruse & Patterson, editors (1973). Most preferred mammalian cells are BSC-40 African green monkey kidney cells, but other cells, such as human 293 cells, VERO and HeLa cells, Chinese hamster ovary (CHO) cell lines, and WI138, BHK, COS-7, CV, and MDCK cells, are also useful.

The invention provides homogeneous compositions of $\alpha_1$-antitrypsin Portland produced by transformed cells as provided herein. Such homogeneous compositions are intended to be comprised of mammalian $\alpha_1$-antitrypsin Portland protein that comprises at least 90% of the protein in such homogenous composition.

The recombinant expression constructs of the present invention are useful in molecular biology to transform cells in vivo in an animal as a method for protecting the animal from viral or other infection in cells that express furin or a furin-like endoprotease activity that can be inhibited by $\alpha_1$-antitrypsin Portland. The invention provides a gene therapy delivery system comprising the recombinant expression constructs of the invention in a configuration that enables safe and efficient introduction of these sequences into appropriate cells and expression of $\alpha_1$-antitrypsin Portland. For such purposes, retroviral vectors as described in U.S. Pat. No. 4,650,764 to Temin & Watanabe or U.S. Pat. No. 4,861,719 to Miller may be employed, for example. The recombinant expression constructs of the invention may also be used in gene therapy carried out homologous recombination. See generally Thomas & Capecchi, 1987, Cell 51: 503–512; Bertling, 1987, Bioscience Reports 7: 107–112; Smithies et al., 1985, Nature 317: 230–234. Additionally, alteration of endogenous $\alpha_1$-antitrypsin sequences to produce $\alpha_1$-antitrypsin Portland in cells carrying such altered $\alpha_1$-antitrypsin sequences can also be achieved using homologous recombination or other techniques. Transgenic animals the tissues of which express the $\alpha_1$-antitrypsin Portland variant are also envisioned as additional objects of this invention.

The invention also provides antibacterial and antiviral methods. The invention provides methods for blocking endoproteolytic activation of bacterial toxins. Bacterial targets of the antibacterial methods provided by this invention include but are not limited to any bacteria that produces an endoproteolytically-activated toxin, such as diptheria toxin produced by *Corynebacterium diptheriae*, exotoxin A of *Pseudomonas aurigenosa*, tetanus toxin, the enterotoxins of *Escherichia coli* and *Vibrio cholerae*, protective antigen of *Bacillus anthracis* and the neurotoxin and C2 toxin of *Clostridium botulinum*. Preferred toxins are those that are proteolytically processed at a consensus furin recognition site (-Arg-Xaa-Xaa-Arg↓-) (SEQ ID No. 8). Preferred embodiments include *Corynebacterium diptheriae* and *Bacillus anthracis*.

Viral targets of antiviral methods provided include but are not limited to picornaviruses (e.g., poliovirus and rhinovirus); orthomyxoviruses (e.g., influenza virus); paramyxoviruses (e.g., measles virus and mumps virus); coronaviruses; rhabdoviruses (e.g., rabies virus and vesicular stomatitis virus); togaviruses (e.g., Semliki Forest virus and yellow fever virus); bunyaviruses (e.g., California encephalitis virus); arenaviruses (e.g., Lassa fever virus); rubella virus; reoviruses (e.g., Colorado tick fever virus); hepatitis viruses; adenoviruses; herpesviruses (e.g., herpes simplex virus); and oncogenic viruses, including papilloma viruses, RNA tumor viruses, or retroviruses, and lentiviruses (e.g., human immune deficiency virus). The most preferred viruses are the human immunodeficiency viruses (HIV-1 and HIV-2).

Cells intended to be protected by the methods provided by this invention include but are not limited to human, canine, bovine, murine, leporine, porcine, ovine, simian, feline, hircine, and equine. The preferred cells are human cells. More preferred cells are human T lymphocytes (T cells), and the most preferred human T cells are those human T cells expressing the cell surface antigen CD4.

The methods of the present invention may be used to treat donated human blood or plasma to protect transfusion recipients from viral infection from contaminating virus. The methods of the present invention may be used to treat human semen to protect embryos derived from such semen, and mothers bearing such embryos or impregnated with such semen, from contaminating virus. In a preferred embodiment, the contaminating virus is HIV-1.

The present invention provides methods for inhibiting viral infection in a human. The invention also provides for treating a human infected with a virus. Another embodiment of the present invention includes methods for treating immunosuppression in a human associated with viral infection. Yet another embodiment of the present invention provides a method of prophylaxis for treating a human exposed to infection with a virus, in particular those directly at risk of infection as a result of intimate contact with humans infected with a virus of tissues or bodily fluids contaminated by a virus. The preferred virus of these embodiments of the invention is HIV-1. The invention provides pharmaceutically acceptable compositions effective for use with the methods provided by the invention comprising the peptides of the invention and a pharmaceutically acceptable carrier.

The invention also provides methods for inhibiting proteolytic processing of a biologically active protein or peptide in a cell comprising contacting such cells with the gene therapy delivery system of the invention. The methods of the invention encompass inhibition of proteolytic processing of any biologically active molecule that is proteolytically processed by furin in vivo or in vitro, including but not limited to peptide hormones, neuropeptides, growth factors, coagulation factors, serum albumin, cell surface receptors, and adhesion molecules. Preferred biologically active proteins are pro-β-nerve growth factor, blood coagulation factor protein Factor IX, pro-von Willibrand factor, complement factor C3 and renin.

Preparation of pharmaceutically acceptable compositions provided by the present invention can be prepared using methods well known to those with skill in the art. Any of the common carriers such as sterile saline solution, plasma, etc., can be utilized for preparing the pharmaceutical compositions provided by the invention. Routes of administration include but are not limited to oral, intravenous, parenteral, rectal, optical, aural and transdermal. The pharmaceutical compositions of the invention may be administered intravenously in any conventional medium for intravenous injection such as an aqueous saline medium, or in blood plasma medium. Such medium may also contain conventional pharmaceutical adjunct materials such as, for example, pharmaceutically acceptable salts to adjust the osmotic pressure, buffers, preservatives and the like. Among the preferred media are normal saline and plasma.

The following Examples illustrate certain aspects of the above-described method and advantageous results. The following examples are shown by way of illustration and not by way of limitation.

EXAMPLE 1

Production of Furin Endoprotease in African Green Monkey Cells In Vitro

Human furin was synthesized for inhibition experiments as described in Bresnahan et al. (J. Cell Biol. 111: 2851–2859) and Molloy et al. (J. Biol. Chem. 267: 16396–14402; both hereby incorporated by reference). Briefly, a furin cDNA (van den Ouweland et al., 1992, Nucleic Acids Res. 18: 664) encoding a truncated but functional furin protein was inserted into the multiple cloning site of a vaccinia virus vector (see Hruby et al., 1986, Meth. Enzymol. 124: 295–309) and used to infect BSC-40 African green monkey kidney cells. The cells were incubated in serum-free defined media for 24 hours and then harvested at 4° C. and disrupted by 20–30 strokes in a Dounce homogenizer (Kontes Glass Co., Vineland, Ohio). The lysate was cleared by low-speed centrifugation (1000 g, 5 min) and the supernatant then subjected to ultracentrifugation at 100,000 g for 1 hr. The pellet was resuspended in 200 μL of a buffer comprising 10 mM HEPES (N-(2-hydroxyethyl)piperazine-N'-(2-ethanesulfonic acid), SIgma Chemical Co., St. Louis, Mo.) and stored at 4° C. until use.

Alternatively, a soluble, truncated derivative of furin lacking the carboxyl-terminal 81 amino acids was used (see Molloy et al., ibid., incorporated by reference, for a more detailed description of this molecule). Briefly, BSC-40 cells were infected with a vaccinia virus vector containing the truncated furin cDNA, grown for 16–18 h in serum-free defined media and then harvested. The cells were disrupted and subjected sequentially to centrifugation at 1000 g and 10,000 g at 4° C. The supernatant was passed through a 0.2 μm filter and then diluted approximately 1:1 with a buffer consisting of 20 mM BisTris (pH 7.0) and 1 mM 2-mercaptoethanol. This mixture was then applied to a Mono Q HR 5/5 fast protein liquid chromatography anion exchange column (Pharmacia LKB Biotechnology Inc.) and the truncated furin derivative eluted with a gradient of 0–750 mM sodium chloride and stored at 4° C. until use.

EXAMPLE 2

In Vitro Mutagenesis and Production of Native and Variant Species of $\alpha_1$-Antitrypsin A novel $\alpha_1$-antitrypsin variant, termed $\alpha_1$-antitrypsin Portland (SEQ ID No.:9), was produced by in vitro mutagenesis of a cloned cDNA encoding the variant $\alpha_1$-antitrypsin Pittsburgh (SEQ ID Nos.: 12 & 13). A full length cDNA encoding $\alpha_1$-antitrypsin Pittsburgh was subcloned into M13mp19 phage using standard techniques (see Sambrook et al., ibid., Chapter 15). The following mutagenesis primer was then annealed to the sequence of single-stranded phage DNA corresponding to codons 372–378 of the $\alpha_1$-antitrypsin Pittsburgh sequence:

5'-TTTTTAGAGCGCATACCCAG-3'
(SEQ ID No.:14)

The underlined sequence encodes the mutagenized codon. After annealing, the mutagenesis primer was extended using the Klenow fragment of *E. coli* DNA polymerase in the presence of the four deoxynucleotide triphosphates. Clones having the mutagenized sequence were then grown and selected in *E. coli,* and DNA sequencing of the appropriate portion of the sequence of selected mutagenized clones was performed to confirm successful mutagenesis. The mutagenized $\alpha_1$-antitrypsin cDNA sequences were then subcloned into vaccinia virus vector pVZneo and used to produce vaccinia virus recombinants as described in Example 1 (and described in more detail in Hayflick et al., 1992, J. Neurosci. 12: 705–717, hereby incorporated by reference).

As a result of mutagenesis, the sequence of $\alpha_1$-antitrypsin Pittsburgh ($Ala_{355}$-Ile-Pro-$Arg_{358}$) (SEQ ID No.:15) was changed to the novel sequence of $\alpha_1$-antitrypsin Portland ($Arg_{355}$-Ile-Pro-$Arg_{358}$) (SEQ ID No.:10). Vaccinia virus constructs containing native $\alpha_1$-antitrypsin (SEQ ID Nos.: 16 & 17), (Ala$_{355}$-Ile-Pro-Met$_{358}$) (SEQ ID No.:7), $\alpha_1$-antitrypsin Pittsburgh (SEQ ID Nos.:12 & 13) and $\alpha_1$-antitrypsin Portland (SEQ ID Nos.:18 & 19) were each used to infect BSC-40 cells. Such infected cells secrete the $\alpha_1$-antitrypsins into the culture media, and native $\alpha_1$-antitrypsin and variants were isolated from culture media from appropriately-infected BSC-40 cells by passage of such media over a Mono Q HR 5/5 high pressure liquid chromatography anion exchange column (Pharmacia LKB Biotechnology Ltd., Stockholm, Sweden) and eluted using a linear gradient (0.05→0.5M) of sodium chloride in 50 mM Tris-HCl (pH 8.0), as described further in Molloy et al. Production of native $\alpha_1$-antitrypsin (Lane 1) and variants Pittsburgh (Lane 2) and Portland (Lane 3) was confirmed by Western blot hybridization (see Sambrook et al., ibid., Chapter 18) as shown in FIG. 1.

EXAMPLE 3

Figure 2:
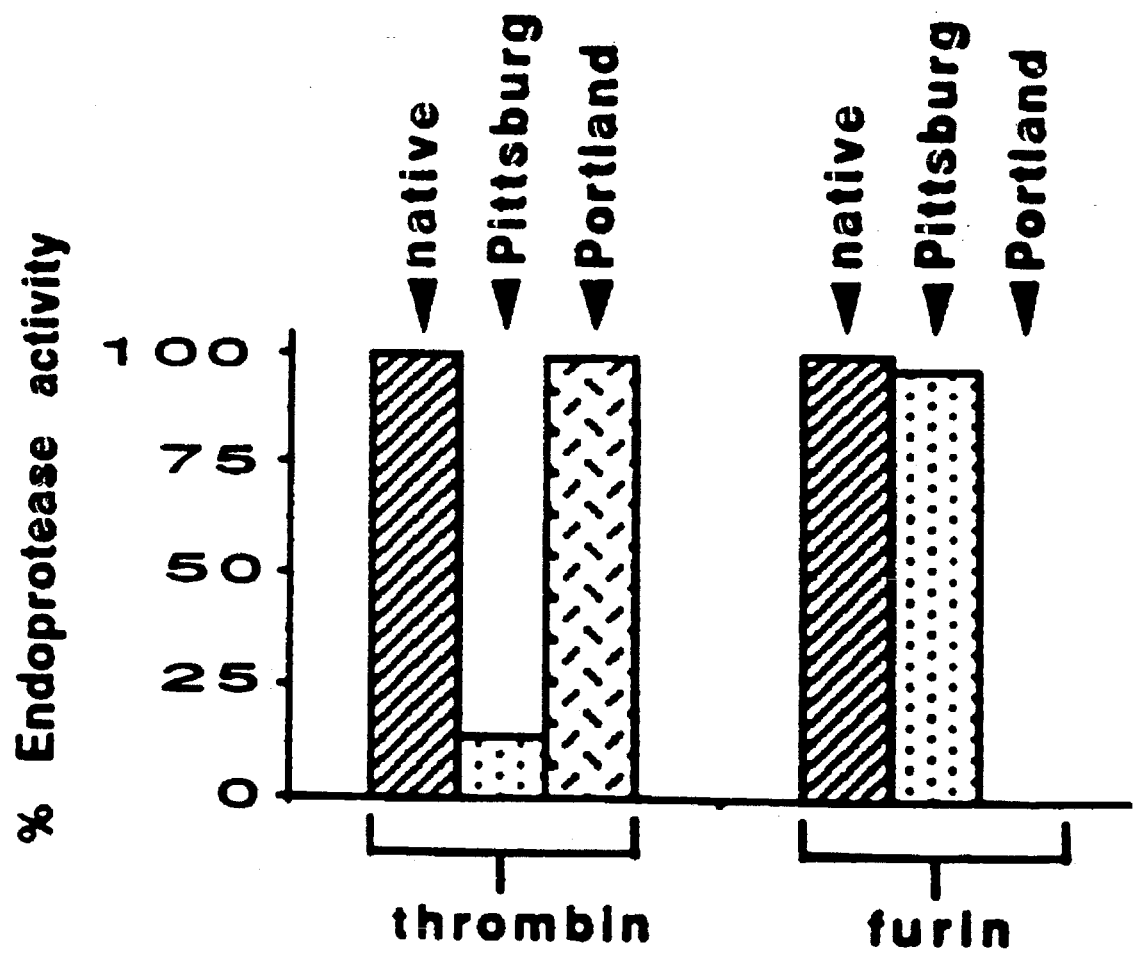
FIG. 2 shows inhibition of thrombin and furin by native $\alpha_1$-antitrypsin (striped bars), $\alpha_1$-antitrypsin Pittsburgh (dotted bars) and $\alpha_1$-antitrypsin Portland (stipled bars) in vitro.

In Vitro Characterization of Furin Endoprotease Inhibition by $\alpha_1$-Antitrypsin Portland $\alpha_1$-antitrypsin and variants Pittsburgh and Portland were assayed for the ability to inhibit furin endoprotease in vitro essentially as described in Molloy et al. (ibid.). Briefly, 25 µL of the resuspended furin preparation described in Example 1 was incubated with each of the $\alpha_1$-antitrypsins (at a final concentration of 10 µg/mL) for 20 min at 37° C. in a buffer comprising 100 mM HEPES (pH 7.5), 1 mM CaCl$_2$, 1 mM 2-mercaptoethanol and 0.5% Triton-X 100. Substrate (N-butoxycarbonyl)-Arg-Val-Arg-Arg-(4-methylcoumaryl-7-amide); Peninsula Laboratories, Belmont, Calif.) was then added to a final concentration of 50 µM and incubated for 30 min at 37° C. The amount of liberated aminomethylcoumarin was then determined by fluorimetry (excitation wavelength=380 nm; emission wavelength=460 nm) using a spectrofluorimeter (Perkin Elmer, Waterbury, Conn., Model LS3). The results of this experiment is shown in FIG. 2. For comparison, each of the $\alpha_1$-antitrypsins were also incubated with thrombin and assayed for thrombin peptidase activity colorometrically using benzoyl-Phe-Val-Arg-(para-nitroanilide) as substrate. These results are also shown in FIG. 2. Native $\alpha_1$-antitrypsin is unable to inhibit either furin or thrombin endoprotease activity (striped bars). $\alpha_1$-antitrypsin Pittsburgh specifically inhibits thrombin but not furin (dotted bars). The novel variant $\alpha_1$-antitrypsin Portland (stipled bars) has no effect on thrombin endoprotease activity, but specifically and essentially quantitatively inhibits furin endoprotease activity.

EXAMPLE 4

In Vivo Characterization of Furin Endoprotease Inhibition by $\alpha_1$-Antitrypsin Portland $\alpha_1$-antitrypsin Portland was assayed for the ability to inhibit furin endoprotease in vivo. BSC-40 cells were co-infected with a vaccinia virus vector encoding the $\alpha_1$-antitrypsin Portland as described in Example 2 and a vaccinia virus vector encoding pro-β-nerve growth factor (β-NGF), a neuropeptide growth factor known to be processed by furin at the consensus furin site -Arg-Ser-Lys-Arg↓- (SEQ ID No.:1) (Bresnahan et al., ibid.) and secreted into the cell growth media. Co-infected cells were incubated in the presence of ($^{35}$S)-methionine for 4 h after infection and the cell media harvested. Media samples were then immunoprecipitated with NGF-specific antibodies and assayed by sodium dodecyl sulfate/polyacrylamide gel electrophoresis (SDS-PAGE, as described in Sambrook et al., ibid.).

Figure 3:
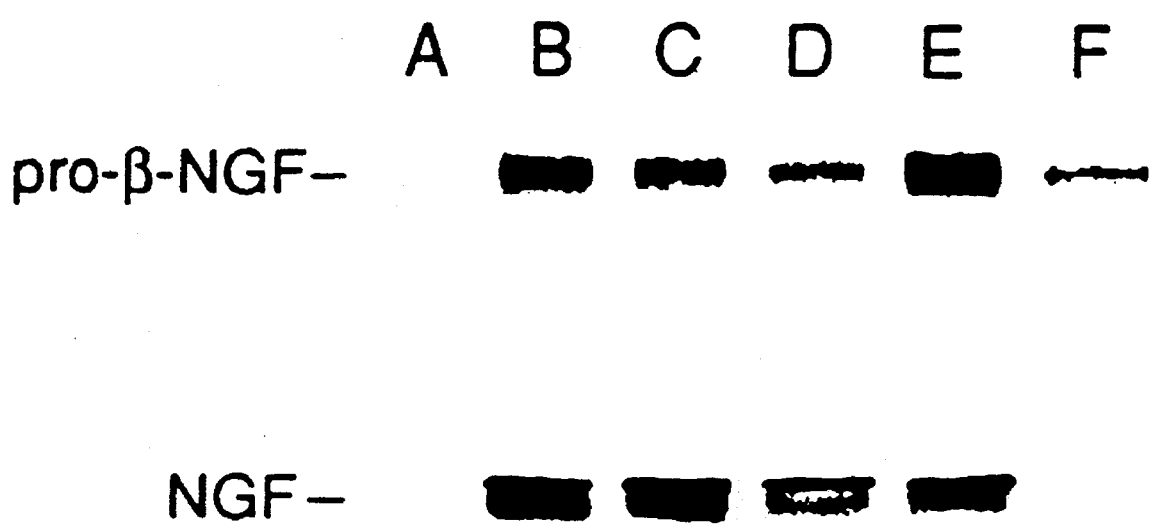
FIG. 3 is an SDS-PAGE analysis of inhibition showing proteolytic processing of pro-β-NGF by $\alpha_1$-antitrypsin and variants.

The results of these experiments are shown in FIG. 3. Cells infected with wild-type vaccinia virus secrete no detectable β-NGF into the culture media (Lane A), whereas cells infected with the vaccinia virus vector encoding β-NGF secrete both processed (13 kilodaltons, kD) and unprocessed (≈35 kD) forms of β-NGF (Lane B); co-infection of such cells with wild-type vaccinia virus has no effect on this pattern of β-NGF production (Lane C). Similarly, BSC-40 cells co-infected with the β-NGF construct and with vaccinia virus constructs encoding native $\alpha_1$-antitrypsin (Lane D) and $\alpha_1$-antitrypsin Pittsburgh (Lane E) also produce both the processed and unprocessed forms of β-NGF. In contrast, cells co-infected with the β-NGF construct and with vaccinia virus constructs encoding $\alpha_1$-antitrypsin Portland (Lane F) produce only the unprocessed form of β-NGF, demonstrating that $\alpha_1$-antitrypsin Portland is capable of inhibiting furin-mediated endoprotease processing of bioactive pro-peptides in vivo.

EXAMPLE 5

Inhibition of Furin-Mediated Processing of Human Immunodeficiency Virus gp160 by $\alpha_1$-Antitrypsin Portland The experiments described in Example 4 were repeated using a vaccinia virus construct encoding the Human Immunodeficiency virus (HIV-1) glycoprotein gp160. This precursor protein is known to be proteolytically processed into two membrane-associated proteins: gp120 (which binds the HIV receptor CD4 on the cell surface of target host cells) and gp41 (which provides a fusogenic activity that mediates vital entry into the cell) in vivo. Proteolytic processing at the furin consensus site -Arg-Glu-Lys-Arg↓- (SEQ ID No.:3) is a necessary step in maturation and release of HIV vital particles. Cell membranes from cells infected with vaccinia virus constructs are isolated as described in Example 1. Proteins from such membrane preparations were resolved by SDS-PAGE and specifically identified by Western blot analysis (see Sambrook et al., ibid., Chapter 18).

Figure 4:
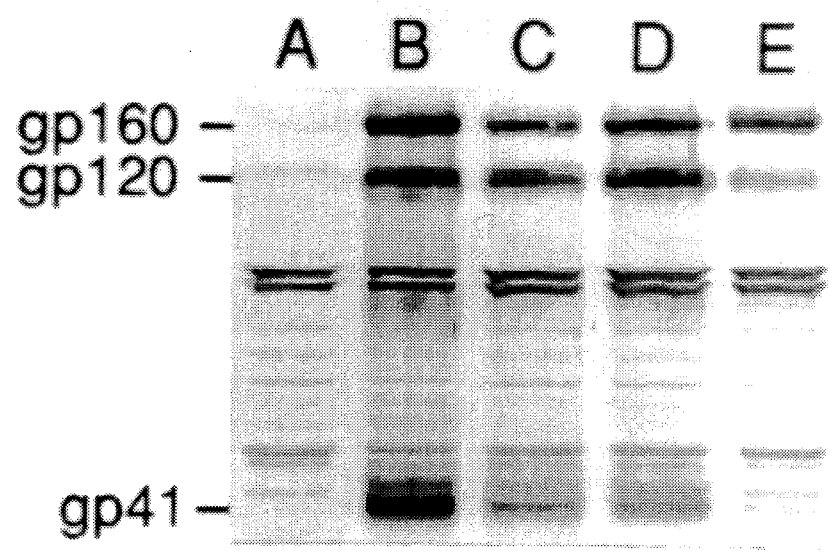
FIG. 4 depicts Western blot analysis showing inhibition of proteolytic processing of HIV gp160 by $\alpha_1$-antitrypsin and variants.

The results of this experiment are shown in FIG. 4. Cells infected with wild-type vaccinia virus produce no detectable HIV-related peptides (Lane A). In cells infected with the vaccinia virus vector encoding gp160, both the unprocessed protein and processing products, gp120 and gp41 are produced (Lane B). BSC-40 cells co-infected with the gp160 construct and with vaccinia virus constructs encoding native $\alpha_1$-antitrypsin (Lane C) and $\alpha_1$-antitrypsin Pittsburgh (Lane D) also produce both unprocessed gp160 and processed gp120 and gp41. Cells co-infected with the gp160 construct and with vaccinia virus constructs encoding $\alpha_1$-antitrypsin Portland (Lane E), on the other hand, produce only unprocessed gp160. These results demonstrate that $\alpha_1$-antitrypsin Portland is capable of inhibiting furin-mediated endoprotease processing of bioactive viral proteins in vivo, and immediately suggest a method for treating viral infection by inhibiting viral protein processing.

Figure 5:
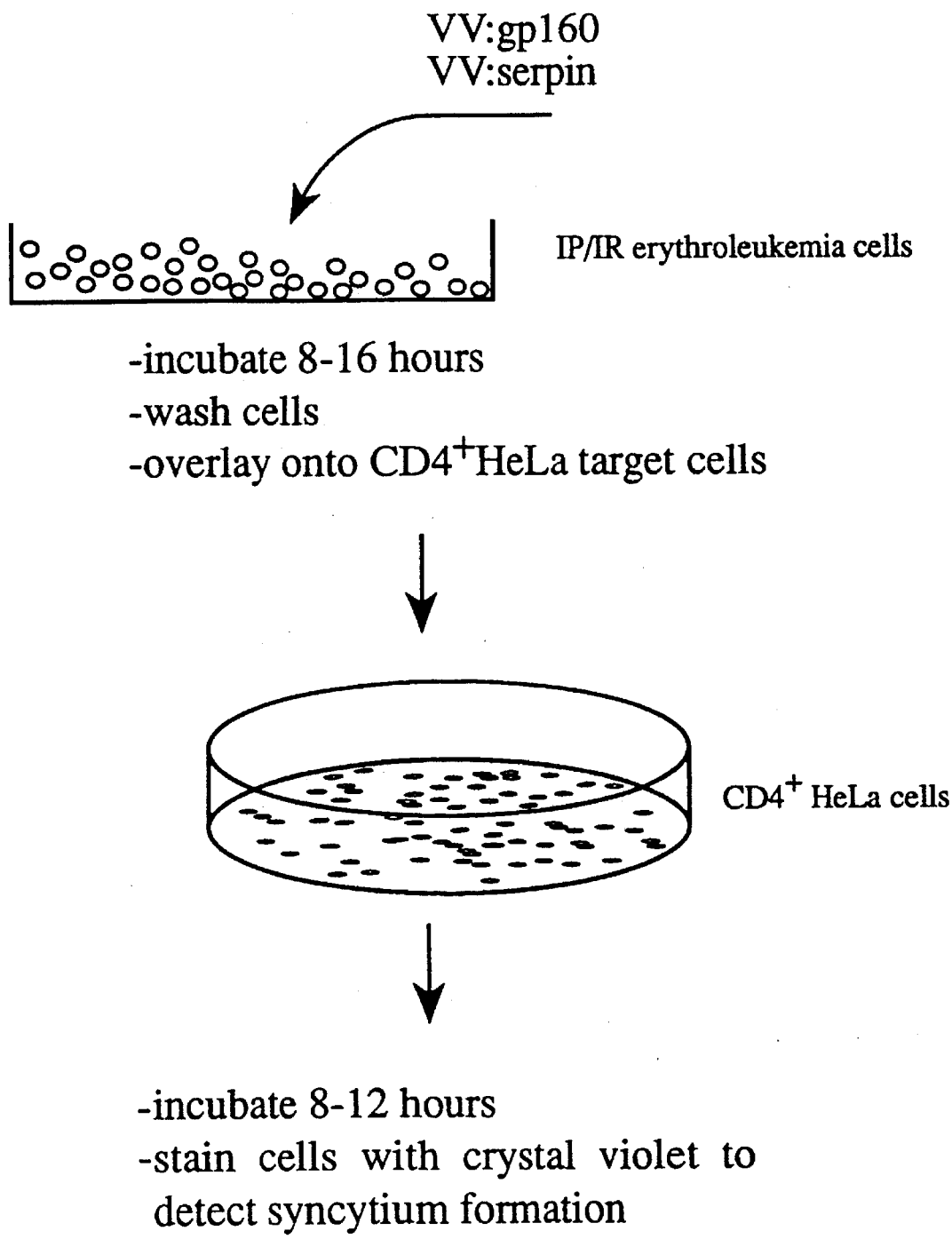

In another series of experiments, $\alpha_1$-antitrypsin Portland-mediated inhibition of proteolytic processing of gp160 was assayed to determine the functional consequences of such inhibition. As described above, processing of gp160 results in the production of gp41, a protein that provides a fusogenic activity important for viral entry into target cells. Expression of gp120 and gp41 on the surface of IP/IR erythroleukemia cells promotes cell fusion and syncytium formation with cells expressing the gp120 target, CD4, at the cell surface. In these experiments, IP/IR cells were co-infected with gp160 and each of the $\alpha_1$-antitrypsins to determine the effect of inhibition of gp160 processing on the fusogenic capacity of the cells. This experimental protocol is shown in FIG. 5. Briefly, IP/IR cells were co-infected with the vaccinia virus gp160 construct, either alone or co-infected with each of the $\alpha_1$-antitrypsin constructs described in Example 2. The cells were incubated for 8–16 hours, collected and then overlaid onto a monolayer of CD4$^+$ human HeLa cells. These cells were incubated for an additional 8–12 hours, and syncytium formation detected by staining with crystal violet and observed by phase-contrast microscopy.

Figure 6:
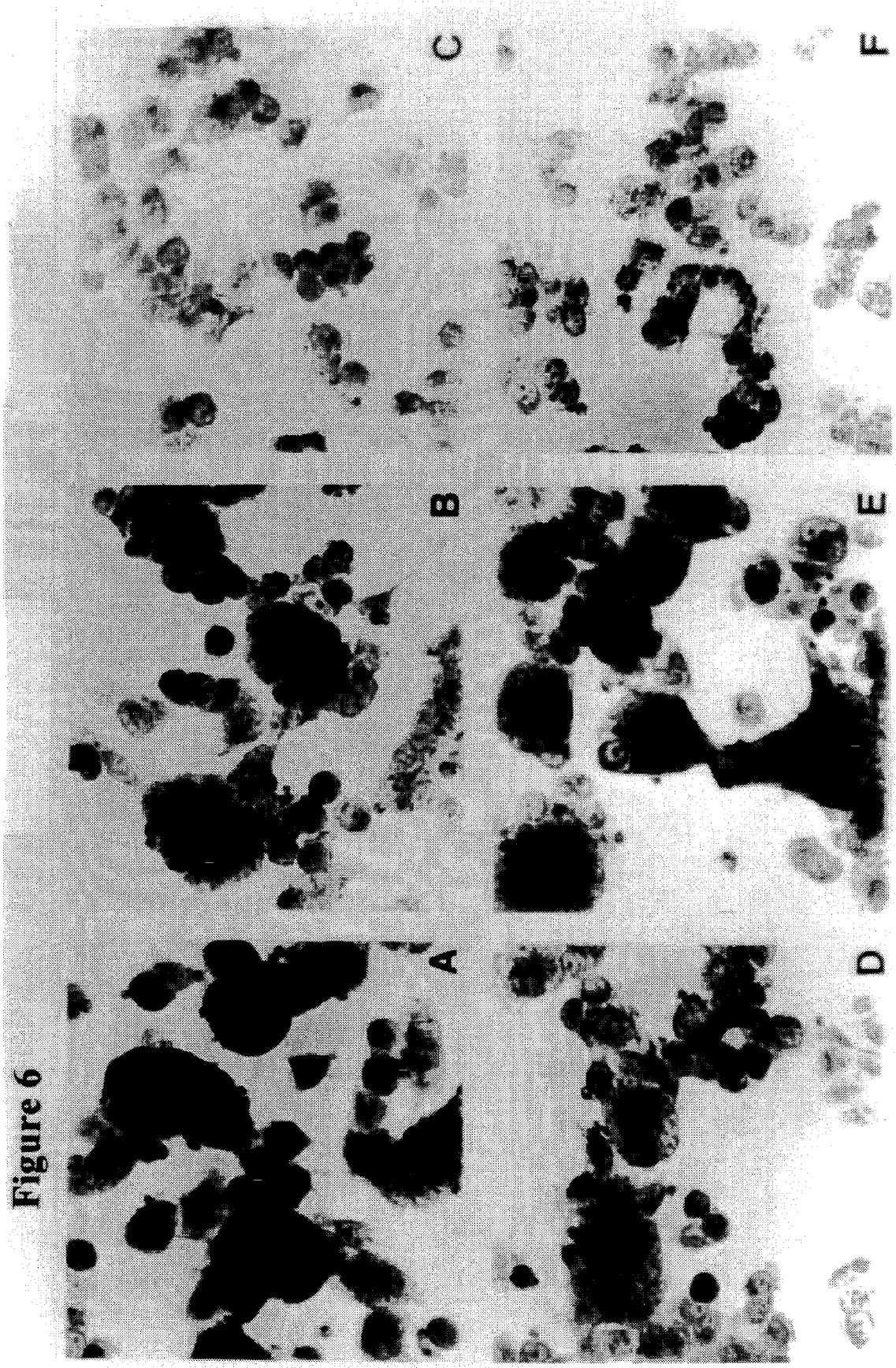

The results of these experiments are shown in FIG. 6. Panel A shows the results of infection of HeLa cells with wild-type vaccina virus; essentially no multinucleated cells are seen in such cells. Panel B shows the results of infection of HeLa cells with vaccina virus recombinants encoding HIV gp 160. Syncytia formation (and hence proper proteolytic processing of gp160 to gp120 and gp41) in these cells is evidenced by the large number of multinucleated cells in the culture. Panels C and D show the results of co-infection of vaccinia virus recombinants encoding gp 160 and native (Panel C) and the Pittsburgh variant (Panel D) of $\alpha_1$-antitrypsin. Co-expression of native or variant Pittsburgh $\alpha_1$-antitrypsin has no effect on syncytia formation caused by gp41. Panel E shows the effect on HIV gp41-mediated syncytia formation of co-expression of gp160 and $\alpha_1$-antitrypsin Portland in HeLa cells. Syncytia formation is completely abolished in these cells, which look identical to cells infected with wild-type vaccinia virus seen in Panel A. These results demonstrate that inhibition of gp160 processing by $\alpha_1$-antitrypsin Portland eliminates the fusogenic activity of viral gp41 and suggests that such inhibition may provide a method for treating HIV infection in vivo and in vitro.

It should be understood that the foregoing disclosure emphasizes certain specific embodiments of the invention and that all modifications or alternatives equivalent thereto are within the spirit and scope of the invention as set forth in the appended claims.

What we claim is:

1. A furin endoprotease inhibitor that is an $\alpha_1$-antitrypsin variant having an amino acid sequence comprising the amino acids -Arg-Xaa-Xaa-Arg-, wherein Xaa is any amino acid, at positions 355–358 of the native $\alpha_1$-antitrypsin amino acid sequence (SEQ ID No.:6).

2. The furin endoprotease inhibitor of claim 1 that is $\alpha_1$-antitrypsin Portland (SEQ ID No.:9).

3. A nucleic acid having a nucleotide sequence that encodes an $\alpha_1$-antitrypsin variant, wherein the amino acid sequence encoded by the nucleic acid has the sequence -Arg-Xaa-Xaa-Arg-, where Xaa is any amino acid, at positions 355–358 of the native $\alpha_1$-antitrypsin amino acid sequence (SEQ ID No.:6).

4. The nucleic acid of claim 3 that encodes $\alpha_1$-antitrypsin Portland (SEQ ID No.:9).

5. A recombinant expression construct comprising a nucleic acid having a nucleotide sequence encoding an $\alpha_1$-antitrypsin variant wherein the amino acid sequence encoded by the nucleotide sequence comprises the amino acids -Arg-Xaa-Xaa-Arg-, wherein Xaa is any amino acid, at positions 355–358 of the native $\alpha_1$-antitrypsin amino acid sequence (SEQ ID No.:6).

6. The recombinant expression construct of claim 5, wherein the $\alpha_1$-antitrypsin variant is $\alpha_1$-antitrypsin Portland (SEQ ID No.:9).

7. A recombinant expression construct comprising the nucleic acid of claim 3, wherein the construct expresses $\alpha_1$-antitrypsin Portland (SEQ ID No.:9) in a culture of transformed cells.

8. A cell culture transformed with the recombinant expression construct of claim 5, wherein the transformed cell culture expresses $\alpha_1$-antitrypsin Portland (SEQ ID No.:9).

9. The cell culture of claim 8 comprising bacterial cells, yeast cells, insect cells or mammalian cells.

10. A homogenous composition of matter comprising $\alpha_1$-antitrypsin Portland (SEQ ID No.:9) produced by the cell culture of claim 8.

11. A furin endoprotease inhibitor according to claim 1 which blocks endoproteolytic activation of a bacterial toxin.

12. The furin endoprotease inhibitor of claim 11 wherein the bacterial toxin is diphtheria toxin of *Corynebacterium diptheriae.*

13. The furin endoprotease inhibitor of claim 11 wherein the bacterial toxin is anthrax toxin of *Bacillus anthracis.*

14. A pharmaceutically acceptable composition comprising a therapeutically effective amount of the furin endoprotease inhibitor of claim 11 and a pharmaceutically acceptable carrier or diluent.

* * * * *

SEQUENCE LISTING ( 1 ) GENERAL INFORMATION:

( i i i ) NUMBER OF SEQUENCES: 21

( 2 ) INFORMATION FOR SEQ ID NO:1:

( i ) SEQUENCE CHARACTERISTICS:
( A ) LENGTH: 4 amino acids
( B ) TYPE: amino acid
( D ) TOPOLOGY: linear ( i i ) MOLECULE TYPE: peptide ( x i ) SEQUENCE DESCRIPTION: SEQ ID NO:1:

Arg Ser Lys Arg
1

( 2 ) INFORMATION FOR SEQ ID NO:2:

( i ) SEQUENCE CHARACTERISTICS:
( A ) LENGTH: 4 amino acids
( B ) TYPE: amino acid
( D ) TOPOLOGY: linear ( i i ) MOLECULE TYPE: peptide ( x i ) SEQUENCE DESCRIPTION: SEQ ID NO:2:

Arg Pro Lys Arg
1

( 2 ) INFORMATION FOR SEQ ID NO:3:

( i ) SEQUENCE CHARACTERISTICS:
( A ) LENGTH: 4 amino acids
( B ) TYPE: amino acid
( D ) TOPOLOGY: linear ( i i ) MOLECULE TYPE: peptide ( x i ) SEQUENCE DESCRIPTION: SEQ ID NO:3:

Arg Glu Lys Arg
1

( 2 ) INFORMATION FOR SEQ ID NO:4:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:4:

Arg Val Arg Arg
    1

( 2 ) INFORMATION FOR SEQ ID NO:5:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 2..3
        ( D ) OTHER INFORMATION: /label=Variable-site
                / note="The amino acid X at position 2 can be any
                amino acid; the amino acid X at position 3 can be
                either arginine or lysine;"

( x i ) SEQUENCE DESCRIPTION: SEQ ID NO:5:

Arg Xaa Xaa Arg
    1

( 2 ) INFORMATION FOR SEQ ID NO:6:

( i ) SEQUENCE CHARACTERISTICS:
        ( A ) LENGTH: 394 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Glu  Asp  Pro  Gln  Gly  Asp  Ala  Ala  Gln  Lys  Thr  Asp  Thr  Ser  His  His
1                   5                        10                       15

Asp  Gln  Asp  His  Pro  Thr  Phe  Asn  Lys  Ile  Thr  Pro  Asn  Leu  Ala  Glu
               20                       25                       30

Phe  Ala  Phe  Ser  Leu  Tyr  Arg  Gln  Leu  Ala  His  Gln  Ser  Asn  Ser  Thr
          35                       40                       45

Asn  Ile  Phe  Phe  Ser  Pro  Val  Ser  Ile  Ala  Thr  Ala  Phe  Ala  Met  Leu
     50                       55                       60

Ser  Leu  Gly  Thr  Lys  Ala  Asp  Thr  His  Asp  Glu  Ile  Leu  Glu  Gly  Leu
65                       70                       75                       80

Asn  Phe  Asn  Leu  Thr  Glu  Ile  Pro  Glu  Ala  Gln  Ile  His  Glu  Gly  Phe
               85                       90                       95

Gln  Glu  Leu  Leu  Arg  Thr  Leu  Asn  Gln  Pro  Asp  Ser  Gln  Leu  Gln  Leu
               100                      105                      110

Thr  Thr  Gly  Asn  Gly  Leu  Phe  Leu  Ser  Gln  Gly  Leu  Lys  Leu  Val  Asp
          115                      120                      125

Lys  Phe  Leu  Glu  Asp  Val  Lys  Lys  Leu  Tyr  His  Ser  Glu  Ala  Phe  Thr
     130                      135                      140

Val  Asn  Phe  Gly  Asp  Thr  Glu  Gln  Ala  Lys  Lys  Gln  Ile  Asn  Asp  Tyr
145                      150                      155                      160
```

```
Val  Glu  Lys  Gly  Thr  Gln  Gly  Lys  Ile  Val  Asp  Leu  Val  Lys  Glu  Leu
               165                      170                     175

Asp  Arg  Asp  Thr  Val  Phe  Ala  Leu  Val  Asn  Tyr  Ile  Phe  Phe  Lys  Gly
               180                      185                     190

Lys  Trp  Glu  Arg  Pro  Phe  Glu  Val  Lys  Asp  Thr  Glu  Glu  Glu  Asp  Phe
          195                      200                     205

His  Val  Asp  Gln  Val  Thr  Thr  Val  Lys  Val  Pro  Met  Met  Lys  Arg  Leu
          210                      215                     220

Gly  Met  Phe  Asn  Ile  Gln  His  Cys  Lys  Lys  Leu  Ser  Ser  Trp  Val  Leu
225                      230                     235                          240

Leu  Met  Lys  Tyr  Leu  Gly  Asn  Ala  Thr  Ala  Ile  Phe  Phe  Leu  Pro  Asp
               245                      250                     255

Glu  Gly  Lys  Leu  Gln  His  Leu  Glu  Asn  Glu  Leu  Thr  His  Asp  Ile  Ile
               260                      265                     270

Thr  Lys  Phe  Leu  Glu  Asn  Glu  Asp  Arg  Arg  Ser  Ala  Ser  Leu  His  Leu
          275                      280                     285

Pro  Lys  Leu  Ser  Ile  Thr  Gly  Thr  Tyr  Asp  Leu  Lys  Ser  Val  Leu  Gly
     290                      295                     300

Gln  Leu  Gly  Ile  Thr  Lys  Val  Phe  Ser  Asn  Gly  Ala  Asp  Leu  Ser  Gly
305                      310                     315                          320

Val  Thr  Glu  Glu  Ala  Pro  Leu  Lys  Leu  Ser  Lys  Ala  Val  His  Lys  Ala
               325                      330                     335

Val  Leu  Thr  Ile  Asp  Glu  Lys  Gly  Thr  Glu  Ala  Ala  Gly  Ala  Met  Phe
               340                      345                     350

Leu  Glu  Ala  Ile  Pro  Met  Ser  Ile  Pro  Pro  Glu  Val  Lys  Phe  Asn  Lys
          355                      360                     365

Pro  Phe  Val  Phe  Leu  Met  Ile  Glu  Gln  Asn  Thr  Lys  Ser  Pro  Leu  Phe
     370                      375                     380

Met  Gly  Lys  Val  Val  Asn  Pro  Thr  Gln  Lys
385                      390
```

( 2 ) INFORMATION FOR SEQ ID NO:7:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:7:

```
Ala  Ile  Pro  Met
1
```

( 2 ) INFORMATION FOR SEQ ID NO:8:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 2..3
        ( D ) OTHER INFORMATION: /label=Variable-site
            / note="Each of the amino acids X can be any amino acid;"

( x i ) SEQUENCE DESCRIPTION: SEQ ID NO:8:

Arg Xaa Xaa Arg
1

(2) INFORMATION FOR SEQ ID NO:9:

(i) SEQUENCE CHARACTERISTICS:
        (A) LENGTH: 394 amino acids
        (B) TYPE: amino acid
        (D) TOPOLOGY: linear (ii) MOLECULE TYPE: protein (ix) FEATURE:
        (A) NAME/KEY: Protein
        (B) LOCATION: 1..394
        (D) OTHER INFORMATION: /label=Variant
            / note="This amino acid sequence is the amino acid
            sequence of the modified alpha-1-antitrypsin
            protein, alpha-1-antitrypsin Portland;"

(xi) SEQUENCE DESCRIPTION: SEQ ID NO:9:

```
Glu Asp Pro Gln Gly Asp Ala Ala Gln Lys Thr Asp Thr Ser His His
1               5                   10                  15

Asp Gln Asp His Pro Thr Phe Asn Lys Ile Thr Pro Asn Leu Ala Glu
            20                  25                  30

Phe Ala Phe Ser Leu Tyr Arg Gln Leu Ala His Gln Ser Asn Ser Thr
        35                  40                  45

Asn Ile Phe Phe Ser Pro Val Ser Ile Ala Thr Ala Phe Ala Met Leu
    50                  55                  60

Ser Leu Gly Thr Lys Ala Asp Thr His Asp Glu Ile Leu Glu Gly Leu
65                  70                  75                  80

Asn Phe Asn Leu Thr Glu Ile Pro Glu Ala Gln Ile His Glu Gly Phe
                85                  90                  95

Gln Glu Leu Leu Arg Thr Leu Asn Gln Pro Asp Ser Gln Leu Gln Leu
            100                 105                 110

Thr Thr Gly Asn Gly Leu Phe Leu Ser Gln Gly Leu Lys Leu Val Asp
        115                 120                 125

Lys Phe Leu Glu Asp Val Lys Lys Leu Tyr His Ser Glu Ala Phe Thr
    130                 135                 140

Val Asn Phe Gly Asp Thr Glu Gln Ala Lys Lys Gln Ile Asn Asp Tyr
145                 150                 155                 160

Val Glu Lys Gly Thr Gln Gly Lys Ile Val Asp Leu Val Lys Glu Leu
                165                 170                 175

Asp Arg Asp Thr Val Phe Ala Leu Val Asn Tyr Ile Phe Phe Lys Gly
            180                 185                 190

Lys Trp Glu Arg Pro Phe Glu Val Lys Asp Thr Glu Glu Glu Asp Phe
        195                 200                 205

His Val Asp Gln Val Thr Thr Val Lys Val Pro Met Met Lys Arg Leu
    210                 215                 220

Gly Met Phe Asn Ile Gln His Cys Lys Lys Leu Ser Ser Trp Val Leu
225                 230                 235                 240

Leu Met Lys Tyr Leu Gly Asn Ala Thr Ala Ile Phe Phe Leu Pro Asp
                245                 250                 255

Glu Gly Lys Leu Gln His Leu Glu Asn Glu Leu Thr His Asp Ile Ile
            260                 265                 270

Thr Lys Phe Leu Glu Asn Glu Asp Arg Arg Ser Ala Ser Leu His Leu
        275                 280                 285

Pro Lys Leu Ser Ile Thr Gly Thr Tyr Asp Leu Lys Ser Val Leu Gly
    290                 295                 300
```

```
Gln  Leu  Gly  Ile  Thr  Lys  Val  Phe  Ser  Asn  Gly  Ala  Asp  Leu  Ser  Gly
305                 310                      315                          320

Val  Thr  Glu  Glu  Ala  Pro  Leu  Lys  Leu  Ser  Lys  Ala  Val  His  Lys  Ala
               325                      330                          335

Val  Leu  Thr  Ile  Asp  Glu  Lys  Gly  Thr  Glu  Ala  Ala  Gly  Ala  Met  Phe
               340                      345                     350

Leu  Glu  Arg  Ile  Pro  Arg  Ser  Ile  Pro  Pro  Glu  Val  Lys  Phe  Asn  Lys
          355                      360                     365

Pro  Phe  Val  Phe  Leu  Met  Ile  Glu  Gln  Asn  Thr  Lys  Ser  Pro  Leu  Phe
     370                 375                      380

Met  Gly  Lys  Val  Val  Asn  Pro  Thr  Gln  Lys
385                      390
```

( 2 ) INFORMATION FOR SEQ ID NO:10:

( i ) SEQUENCE CHARACTERISTICS:
    ( A ) LENGTH: 4 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:10:

```
Arg  Ile  Pro  Arg
1
```

( 2 ) INFORMATION FOR SEQ ID NO:11:

( i ) SEQUENCE CHARACTERISTICS:
    ( A ) LENGTH: 394 amino acids
    ( B ) TYPE: amino acid
    ( D ) TOPOLOGY: linear ( i i ) MOLECULE TYPE: protein ( i x ) FEATURE:
    ( A ) NAME/KEY: Protein
    ( B ) LOCATION: 1..394
    ( D ) OTHER INFORMATION: /label=Variants
          / note="This amino acid sequence is the amino acid
          sequence of the modified alpha-1-antitrypsin
          variant, alpha-1-antitrypsin Pittsburgh "

( x i ) SEQUENCE DESCRIPTION: SEQ ID NO:11:

```
Glu  Asp  Pro  Gln  Gly  Asp  Ala  Ala  Gln  Lys  Thr  Asp  Thr  Ser  His  His
1                   5                        10                          15

Asp  Gln  Asp  His  Pro  Thr  Phe  Asn  Lys  Ile  Thr  Pro  Asn  Leu  Ala  Glu
               20                      25                          30

Phe  Ala  Phe  Ser  Leu  Tyr  Arg  Gln  Leu  Ala  His  Gln  Ser  Asn  Ser  Thr
          35                      40                      45

Asn  Ile  Phe  Phe  Ser  Pro  Val  Ser  Ile  Ala  Thr  Ala  Phe  Ala  Met  Leu
     50                      55                      60

Ser  Leu  Gly  Thr  Lys  Ala  Asp  Thr  His  Asp  Glu  Ile  Leu  Glu  Gly  Leu
65                      70                      75                          80

Asn  Phe  Asn  Leu  Thr  Glu  Ile  Pro  Glu  Ala  Gln  Ile  His  Glu  Gly  Phe
               85                      90                          95

Gln  Glu  Leu  Leu  Arg  Thr  Leu  Asn  Gln  Pro  Asp  Ser  Gln  Leu  Gln  Leu
               100                     105                         110

Thr  Thr  Gly  Asn  Gly  Leu  Phe  Leu  Ser  Gln  Gly  Leu  Lys  Leu  Val  Asp
          115                     120                     125

Lys  Phe  Leu  Glu  Asp  Val  Lys  Lys  Leu  Tyr  His  Ser  Glu  Ala  Phe  Thr
     130                     135                     140
```

| | | | | | | | | | | | | | | | |
|---|---|---|---|---|---|---|---|---|---|---|---|---|---|---|---|
|Val|Asn|Phe|Gly|Asp|Thr|Glu|Gln|Ala|Lys|Lys|Gln|Ile|Asn|Asp|Tyr|
|145| | | | |150| | | |155| | | | |160| |
|Val|Glu|Lys|Gly|Thr|Gln|Gly|Lys|Ile|Val|Asp|Leu|Val|Lys|Glu|Leu|
| | | | |165| | | |170| | | | |175| | |
|Asp|Arg|Asp|Thr|Val|Phe|Ala|Leu|Val|Asn|Tyr|Ile|Phe|Phe|Lys|Gly|
| | | |180| | | |185| | | | |190| | | |
|Lys|Trp|Glu|Arg|Pro|Phe|Glu|Val|Lys|Asp|Thr|Glu|Glu|Glu|Asp|Phe|
| | |195| | | |200| | | |205| | | | | |
|His|Val|Asp|Gln|Val|Thr|Thr|Val|Lys|Val|Pro|Met|Met|Lys|Arg|Leu|
|210| | | | |215| | | | |220| | | | | |
|Gly|Met|Phe|Asn|Ile|Gln|His|Cys|Lys|Lys|Leu|Ser|Ser|Trp|Val|Leu|
|225| | | |230| | | | |235| | | | |240| |
|Leu|Met|Lys|Tyr|Leu|Gly|Asn|Ala|Thr|Ala|Ile|Phe|Phe|Leu|Pro|Asp|
| | | |245| | | | |250| | | | |255| | |
|Glu|Gly|Lys|Leu|Gln|His|Leu|Glu|Asn|Glu|Leu|Thr|His|Asp|Ile|Ile|
| | |260| | | | |265| | | | |270| | | |
|Thr|Lys|Phe|Leu|Glu|Asn|Glu|Asp|Arg|Arg|Ser|Ala|Ser|Leu|His|Leu|
| |275| | | | |280| | | | |285| | | | |
|Pro|Lys|Leu|Ser|Ile|Thr|Gly|Thr|Tyr|Asp|Leu|Lys|Ser|Val|Leu|Gly|
|290| | | | |295| | | |300| | | | | | |
|Gln|Leu|Gly|Ile|Thr|Lys|Val|Phe|Ser|Asn|Gly|Ala|Asp|Leu|Ser|Gly|
|305| | | |310| | | |315| | | | | |320| |
|Val|Thr|Glu|Glu|Ala|Pro|Leu|Lys|Leu|Ser|Lys|Ala|Val|His|Lys|Ala|
| | | |325| | | |330| | | | |335| | | |
|Val|Leu|Thr|Ile|Asp|Glu|Lys|Gly|Thr|Glu|Ala|Ala|Gly|Ala|Met|Phe|
| | |340| | | |345| | | |350| | | | | |
|Leu|Glu|Ala|Ile|Pro|Arg|Ser|Ile|Pro|Pro|Glu|Val|Lys|Phe|Asn|Lys|
| |355| | | |360| | | | |365| | | | | |
|Pro|Phe|Val|Phe|Leu|Met|Ile|Glu|Gln|Asn|Thr|Lys|Ser|Pro|Leu|Phe|
|370| | | |375| | | | |380| | | | | | |
|Met|Gly|Lys|Val|Val|Asn|Pro|Thr|Gln|Lys| | | | | | |
|385| | | |390| | | | | | | | | | | |

(2) INFORMATION FOR SEQ ID NO:12:

(i) SEQUENCE CHARACTERISTICS:
        (A) LENGTH: 1356 base pairs
        (B) TYPE: nucleic acid
        (C) STRANDEDNESS: unknown
        (D) TOPOLOGY: linear (ii) MOLECULE TYPE: protein (ix) FEATURE:
        (A) NAME/KEY: CDS
        (B) LOCATION: 34..1278
        (D) OTHER INFORMATION: /product="alpha-1-antitrypsin variant Pittsburgh"
        / standard_name="alpha-1-antitrypsin Pittsburgh"

(xi) SEQUENCE DESCRIPTION: SEQ ID NO:12:

```
GCACCACCAC TGACCTGGGA CAGTGAATCG ACA ATG CCG TCT TCT GTC TCG TGG        54
                                    Met Pro Ser Ser Val Ser Trp
                                     1               5

GGC ATC CTC CTG CTG GCA GGC CTG TGC TGC CTG GTC CCT GTC TCC CTG        102
Gly Ile Leu Leu Leu Ala Gly Leu Cys Cys Leu Val Pro Val Ser Leu
         10                  15                  20

GCT GAG GAT CCC CAG GGA GAT GCT GCC CAG AAG ACA GAT ACA TCC CAC        150
Ala Glu Asp Pro Gln Gly Asp Ala Ala Gln Lys Thr Asp Thr Ser His
 25                  30                  35
```

| | | | | | | | | | | | | | | | | |
|---|---|---|---|---|---|---|---|---|---|---|---|---|---|---|---|---|
| CAT | GAT | CAG | GAT | CAC | CCA | ACC | TTC | AAC | AAG | ATC | ACC | CCC | AAC | CTG | GCT | 198 |
| His | Asp | Gln | Asp | His | Pro | Thr | Phe | Asn | Lys | Ile | Thr | Pro | Asn | Leu | Ala | |
| 40 | | | | 45 | | | | | 50 | | | | | | 55 | |
| GAG | TTC | GCC | TTC | AGC | CTA | TAC | CGC | CAG | CTG | GCA | CAC | CAG | TCC | AAC | AGC | 246 |
| Glu | Phe | Ala | Phe | Ser | Leu | Tyr | Arg | Gln | Leu | Ala | His | Gln | Ser | Asn | Ser | |
| | | | | 60 | | | | | 65 | | | | | 70 | | |
| ACC | AAT | ATT | TTC | TTC | TCC | CCA | GTG | AGC | ATC | GCT | ACA | GCC | TTT | GCA | ATG | 294 |
| Thr | Asn | Ile | Phe | Phe | Ser | Pro | Val | Ser | Ile | Ala | Thr | Ala | Phe | Ala | Met | |
| | | | 75 | | | | | 80 | | | | | 85 | | | |
| CTC | TCC | CTG | GGG | ACC | AAG | GCT | GAC | ACT | CAC | GAT | GAA | ATC | CTG | GAG | GGC | 342 |
| Leu | Ser | Leu | Gly | Thr | Lys | Ala | Asp | Thr | His | Asp | Glu | Ile | Leu | Glu | Gly | |
| | | 90 | | | | | 95 | | | | | 100 | | | | |
| CTG | AAT | TTC | AAC | CTC | ACG | GAG | ATT | CCG | GAG | CCT | CAG | ATC | CAT | GAA | GGC | 390 |
| Leu | Asn | Phe | Asn | Leu | Thr | Glu | Ile | Pro | Glu | Pro | Gln | Ile | His | Glu | Gly | |
| | 105 | | | | | 110 | | | | | 115 | | | | | |
| TTC | CAG | GAA | CTC | CTC | CGT | ACC | CTC | AAC | CAG | CTC | CAG | CTG | ACC | ACC | GGC | 438 |
| Phe | Gln | Glu | Leu | Leu | Arg | Thr | Leu | Asn | Gln | Leu | Gln | Leu | Thr | Thr | Gly | |
| 120 | | | | | 125 | | | | | 130 | | | | | 135 | |
| AAT | GGC | CTG | TTC | CTC | AGC | GAG | GGC | CTG | AAG | CTA | GTG | GAT | AAG | TTT | TTG | 486 |
| Asn | Gly | Leu | Phe | Leu | Ser | Glu | Gly | Leu | Lys | Leu | Val | Asp | Lys | Phe | Leu | |
| | | | | 140 | | | | | 145 | | | | | 150 | | |
| GAG | GAT | GTT | AAA | AAG | TTG | TAC | CAC | TCA | GAA | GCC | TTC | ACT | GTC | AAC | TTC | 534 |
| Glu | Asp | Val | Lys | Lys | Leu | Tyr | His | Ser | Glu | Ala | Phe | Thr | Val | Asn | Phe | |
| | | | 155 | | | | | 160 | | | | | 165 | | | |
| GGG | GAC | ACC | GAA | GAG | GCC | AAG | AAA | CAG | ATC | AAC | GAT | TAC | GTG | GAG | AAG | 582 |
| Gly | Asp | Thr | Glu | Glu | Ala | Lys | Lys | Gln | Ile | Asn | Asp | Tyr | Val | Glu | Lys | |
| | | 170 | | | | | 175 | | | | | 180 | | | | |
| GGT | ACT | CAA | GGG | AAA | ATT | GTG | GAT | TTG | GTC | AAG | GAG | CTT | GAC | AGA | GAC | 630 |
| Gly | Thr | Gln | Gly | Lys | Ile | Val | Asp | Leu | Val | Lys | Glu | Leu | Asp | Arg | Asp | |
| | 185 | | | | | 190 | | | | | 195 | | | | | |
| ACA | GTT | TTT | GCT | CTG | GTG | AAT | TAC | ATC | TTC | TTT | AAA | GGC | AAA | TGG | GAG | 678 |
| Thr | Val | Phe | Ala | Leu | Val | Asn | Tyr | Ile | Phe | Phe | Lys | Gly | Lys | Trp | Glu | |
| 200 | | | | | 205 | | | | | 210 | | | | | 215 | |
| AGA | CCC | TTT | GAA | GTC | AAG | GAC | ACC | GAG | GAA | GAG | GAC | TTC | CAC | GTG | GAC | 726 |
| Arg | Pro | Phe | Glu | Val | Lys | Asp | Thr | Glu | Glu | Glu | Asp | Phe | His | Val | Asp | |
| | | | | 220 | | | | | 225 | | | | | 230 | | |
| CAG | GTG | ACC | ACC | GTG | AAG | GTG | CCT | ATG | ATG | AAG | CGT | TTA | GGC | ATG | TTT | 774 |
| Gln | Val | Thr | Thr | Val | Lys | Val | Pro | Met | Met | Lys | Arg | Leu | Gly | Met | Phe | |
| | | | 235 | | | | | 240 | | | | | 245 | | | |
| AAC | ATC | CAG | CAC | TGT | AAG | AAG | CTG | TCC | AGC | TGG | GTG | CTG | CTG | ATG | AAA | 822 |
| Asn | Ile | Gln | His | Cys | Lys | Lys | Leu | Ser | Ser | Trp | Val | Leu | Leu | Met | Lys | |
| | | 250 | | | | | 255 | | | | | 260 | | | | |
| TAC | CTG | GGC | AAT | GCC | ACC | GCC | ATG | TTC | TTC | CTG | CCT | GAT | GAG | GGG | AAA | 870 |
| Tyr | Leu | Gly | Asn | Ala | Thr | Ala | Met | Phe | Phe | Leu | Pro | Asp | Glu | Gly | Lys | |
| | 265 | | | | | 270 | | | | | 275 | | | | | |
| CTA | CAG | CAC | CTG | GAA | AAT | GAA | CTC | ACC | CAC | GAT | ATC | ATC | ACC | AAG | TTC | 918 |
| Leu | Gln | His | Leu | Glu | Asn | Glu | Leu | Thr | His | Asp | Ile | Ile | Thr | Lys | Phe | |
| 280 | | | | | 285 | | | | | 290 | | | | | 295 | |
| CTG | GAA | AAT | GAA | GAC | AGA | AGG | TCT | GCC | AGC | TTA | CAT | TTA | CCC | AAA | CTG | 966 |
| Leu | Glu | Asn | Glu | Asp | Arg | Arg | Ser | Ala | Ser | Leu | His | Leu | Pro | Lys | Leu | |
| | | | | 300 | | | | | 305 | | | | | 310 | | |
| TCC | ATT | ACT | GGA | ACC | TAT | GAT | CTG | AAG | AGC | GTC | CTG | GGT | CAA | CTG | GGC | 1014 |
| Ser | Ile | Thr | Gly | Thr | Tyr | Asp | Leu | Lys | Ser | Val | Leu | Gly | Gln | Leu | Gly | |
| | | | 315 | | | | | 320 | | | | | 325 | | | |
| ATC | ACT | AAG | GTC | TTC | AGC | AAT | GGG | GCT | GAC | CTC | TCC | GGG | GTC | ACA | GAG | 1062 |
| Ile | Thr | Lys | Val | Phe | Ser | Asn | Gly | Ala | Asp | Leu | Ser | Gly | Val | Thr | Glu | |
| | | 330 | | | | | 335 | | | | | 340 | | | | |
| GAG | GCA | CCC | CTG | AAG | CTC | TCC | AAG | GCC | GTG | CAT | AAG | GCT | GTG | CTG | ACC | 1110 |
| Glu | Ala | Pro | Leu | Lys | Leu | Ser | Lys | Ala | Val | His | Lys | Ala | Val | Leu | Thr | |
| | 345 | | | | | 350 | | | | | 355 | | | | | |

| ATC | GAC | GAG | AAA | GGG | ACT | GAA | GCT | GCT | GGG | GCC | ATG | TTT | TTA | GAG | GCC | 1158 |
| Ile | Asp | Glu | Lys | Gly | Thr | Glu | Ala | Ala | Gly | Ala | Met | Phe | Leu | Glu | Ala | |
| 360 | | | | | 365 | | | | | 370 | | | | | 375 | |

| ATA | CCC | AGG | TCT | ATC | CCC | CCC | GAG | GTC | AAG | TTC | AAC | AAA | CCC | TTT | GTC | 1206 |
| Ile | Pro | Arg | Ser | Ile | Pro | Pro | Glu | Val | Lys | Phe | Asn | Lys | Pro | Phe | Val | |
| | | | | 380 | | | | | 385 | | | | | 390 | | |

| TTC | TTA | ATG | ATT | GAA | CAA | AAT | ACC | AAG | TCT | CCC | CTC | TTC | ATG | GGA | AAA | 1254 |
| Phe | Leu | Met | Ile | Glu | Gln | Asn | Thr | Lys | Ser | Pro | Leu | Phe | Met | Gly | Lys | |
| | | | 395 | | | | | 400 | | | | | 405 | | | |

| GTG | GTG | AAT | CCC | ACC | CAA | AAA | TAACTGCTCG | CTCCTCAACC | CCTCCCCTCC | 1305 |
| Val | Val | Asn | Pro | Thr | Gln | Lys | | | | |
| | | | 410 | | | 415 | | | | |

ATCCCTGGCC CCCTCCCTGG ATGACATTAA AGAAGGGTTG AGCTGGAAAA A    1356

( 2 ) INFORMATION FOR SEQ ID NO:13:

( i ) SEQUENCE CHARACTERISTICS:
        ( A ) LENGTH: 414 amino acids
        ( B ) TYPE: amino acid
        ( D ) TOPOLOGY: linear ( i i ) MOLECULE TYPE: protein ( x i ) SEQUENCE DESCRIPTION: SEQ ID NO:13:

| Met | Pro | Ser | Ser | Val | Ser | Trp | Gly | Ile | Leu | Leu | Leu | Ala | Gly | Leu | Cys |
| 1 | | | | 5 | | | | | 10 | | | | | 15 | |

| Cys | Leu | Val | Pro | Val | Ser | Leu | Ala | Glu | Asp | Pro | Gln | Gly | Asp | Ala | Ala |
| | | | 20 | | | | | 25 | | | | | 30 | | |

| Gln | Lys | Thr | Asp | Thr | Ser | His | His | Asp | Gln | Asp | His | Pro | Thr | Phe | Asn |
| | | | 35 | | | | | 40 | | | | | 45 | | |

| Lys | Ile | Thr | Pro | Asn | Leu | Ala | Glu | Phe | Ala | Phe | Ser | Leu | Tyr | Arg | Gln |
| | 50 | | | | | 55 | | | | | 60 | | | | |

| Leu | Ala | His | Gln | Ser | Asn | Ser | Thr | Asn | Ile | Phe | Phe | Ser | Pro | Val | Ser |
| 65 | | | | | 70 | | | | | 75 | | | | | 80 |

| Ile | Ala | Thr | Ala | Phe | Ala | Met | Leu | Ser | Leu | Gly | Thr | Lys | Ala | Asp | Thr |
| | | | | 85 | | | | | 90 | | | | | 95 | |

| His | Asp | Glu | Ile | Leu | Glu | Gly | Leu | Asn | Phe | Asn | Leu | Thr | Glu | Ile | Pro |
| | | | 100 | | | | | 105 | | | | | 110 | | |

| Glu | Pro | Gln | Ile | His | Glu | Gly | Phe | Gln | Glu | Leu | Leu | Arg | Thr | Leu | Asn |
| | | | 115 | | | | | 120 | | | | | 125 | | |

| Gln | Leu | Gln | Leu | Thr | Thr | Gly | Asn | Gly | Leu | Phe | Leu | Ser | Glu | Gly | Leu |
| | 130 | | | | | 135 | | | | | 140 | | | | |

| Lys | Leu | Val | Asp | Lys | Phe | Leu | Glu | Asp | Val | Lys | Lys | Leu | Tyr | His | Ser |
| 145 | | | | | 150 | | | | | 155 | | | | | 160 |

| Glu | Ala | Phe | Thr | Val | Asn | Phe | Gly | Asp | Thr | Glu | Glu | Ala | Lys | Lys | Gln |
| | | | | 165 | | | | | 170 | | | | | 175 | |

| Ile | Asn | Asp | Tyr | Val | Glu | Lys | Gly | Thr | Gln | Gly | Lys | Ile | Val | Asp | Leu |
| | | | 180 | | | | | 185 | | | | | 190 | | |

| Val | Lys | Glu | Leu | Asp | Arg | Asp | Thr | Val | Phe | Ala | Leu | Val | Asn | Tyr | Ile |
| | | 195 | | | | | 200 | | | | | 205 | | | |

| Phe | Phe | Lys | Gly | Lys | Trp | Glu | Arg | Pro | Phe | Glu | Val | Lys | Asp | Thr | Glu |
| | 210 | | | | | 215 | | | | | 220 | | | | |

| Glu | Glu | Asp | Phe | His | Val | Asp | Gln | Val | Thr | Thr | Val | Lys | Val | Pro | Met |
| 225 | | | | | 230 | | | | | 235 | | | | | 240 |

| Met | Lys | Arg | Leu | Gly | Met | Phe | Asn | Ile | Gln | His | Cys | Lys | Lys | Leu | Ser |
| | | | | 245 | | | | | 250 | | | | | 255 | |

| Ser | Trp | Val | Leu | Leu | Met | Lys | Tyr | Leu | Gly | Asn | Ala | Thr | Ala | Met | Phe |
| | | | 260 | | | | | 265 | | | | | 270 | | |

| | | | | | | | | | | | | | | |
|---|---|---|---|---|---|---|---|---|---|---|---|---|---|---|
| Phe | Leu | Pro | Asp | Glu | Gly | Lys | Leu | Gln | His | Leu | Glu | Asn | Glu | Leu | Thr |
| | | 275 | | | | | 280 | | | | 285 | | | | |
| His | Asp | Ile | Ile | Thr | Lys | Phe | Leu | Glu | Asn | Glu | Asp | Arg | Arg | Ser | Ala |
| | 290 | | | | | 295 | | | | | 300 | | | | |
| Ser | Leu | His | Leu | Pro | Lys | Leu | Ser | Ile | Thr | Gly | Thr | Tyr | Asp | Leu | Lys |
| 305 | | | | | 310 | | | | | 315 | | | | | 320 |
| Ser | Val | Leu | Gly | Gln | Leu | Gly | Ile | Thr | Lys | Val | Phe | Ser | Asn | Gly | Ala |
| | | | | 325 | | | | | 330 | | | | | 335 | |
| Asp | Leu | Ser | Gly | Val | Thr | Glu | Glu | Ala | Pro | Leu | Lys | Leu | Ser | Lys | Ala |
| | | | 340 | | | | | 345 | | | | | 350 | | |
| Val | His | Lys | Ala | Val | Leu | Thr | Ile | Asp | Glu | Lys | Gly | Thr | Glu | Ala | Ala |
| | | 355 | | | | | 360 | | | | | 365 | | | |
| Gly | Ala | Met | Phe | Leu | Glu | Ala | Ile | Pro | Arg | Ser | Ile | Pro | Pro | Glu | Val |
| | 370 | | | | | 375 | | | | | 380 | | | | |
| Lys | Phe | Asn | Lys | Pro | Phe | Val | Phe | Leu | Met | Ile | Glu | Gln | Asn | Thr | Lys |
| 385 | | | | | 390 | | | | | 395 | | | | | 400 |
| Ser | Pro | Leu | Phe | Met | Gly | Lys | Val | Val | Asn | Pro | Thr | Gln | Lys | | |
| | | | | 405 | | | | | 410 | | | | | | |

( 2 ) INFORMATION FOR SEQ ID NO:14:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:14:

TTTTTAGAGC GCATACCCAG                        20

( 2 ) INFORMATION FOR SEQ ID NO:15:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:15:

Ala  Ile  Pro  Arg
    1

( 2 ) INFORMATION FOR SEQ ID NO:16:

( i ) SEQUENCE CHARACTERISTICS:
        ( A ) LENGTH: 1356 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 34..1278
        ( D ) OTHER INFORMATION: /product="alpha-1-antitrypsin
            wild-type sequence"
        / standard_name="alpha-1-antitrypsin"

( x i ) SEQUENCE DESCRIPTION: SEQ ID NO:16:

```
GCACCACCAC TGACCTGGGA CAGTGAATCG ACA ATG CCG TCT TCT GTC TCG TGG        54
                                     Met Pro Ser Ser Val Ser Trp
                                      1               5

GGC ATC CTC CTG CTG GCA GGC CTG TGC TGC CTG GTC CCT GTC TCC CTG        102
Gly Ile Leu Leu Leu Ala Gly Leu Cys Cys Leu Val Pro Val Ser Leu
         10              15                  20

GCT GAG GAT CCC CAG GGA GAT GCT GCC CAG AAG ACA GAT ACA TCC CAC        150
Ala Glu Asp Pro Gln Gly Asp Ala Ala Gln Lys Thr Asp Thr Ser His
    25                  30                  35

CAT GAT CAG GAT CAC CCA ACC TTC AAC AAG ATC ACC CCC AAC CTG GCT        198
His Asp Gln Asp His Pro Thr Phe Asn Lys Ile Thr Pro Asn Leu Ala
40                  45                  50                  55

GAG TTC GCC TTC AGC CTA TAC CGC CAG CTG GCA CAC CAG TCC AAC AGC        246
Glu Phe Ala Phe Ser Leu Tyr Arg Gln Leu Ala His Gln Ser Asn Ser
                60                  65                  70

ACC AAT ATC TTC TTC TCC CCA GTG AGC ATC GCT ACA GCC TTT GCA ATG        294
Thr Asn Ile Phe Phe Ser Pro Val Ser Ile Ala Thr Ala Phe Ala Met
            75                  80                  85

CTC TCC CTG GGG ACC AAG GCT GAC ACT CAC GAT GAA ATC CTG GAG GGC        342
Leu Ser Leu Gly Thr Lys Ala Asp Thr His Asp Glu Ile Leu Glu Gly
        90                  95                  100

CTG AAT TTC AAC CTC ACG GAG ATT CCG GAG CCT CAG ATC CAT GAA GGC        390
Leu Asn Phe Asn Leu Thr Glu Ile Pro Glu Pro Gln Ile His Glu Gly
105                 110                 115

TTC CAG GAA CTC CTC CGT ACC CTC AAC CAG CTC CAG CTG ACC ACC GGC        438
Phe Gln Glu Leu Leu Arg Thr Leu Asn Gln Leu Gln Leu Thr Thr Gly
120                 125                 130                 135

AAT GGC CTG TTC CTC AGC GAG GGC CTG AAG CTA GTG GAT AAG TTT TTG        486
Asn Gly Leu Phe Leu Ser Glu Gly Leu Lys Leu Val Asp Lys Phe Leu
                140                 145                 150

GAG GAT GTT AAA AAG TTG TAC CAC TCA GAA GCC TTC ACT GTC AAC TTC        534
Glu Asp Val Lys Lys Leu Tyr His Ser Glu Ala Phe Thr Val Asn Phe
            155                 160                 165

GGG GAC ACC GAA GAG GCC AAG AAA CAG ATC AAC GAT TAC GTG GAG AAG        582
Gly Asp Thr Glu Glu Ala Lys Lys Gln Ile Asn Asp Tyr Val Glu Lys
        170                 175                 180

GGT ACT CAA GGG AAA ATT GTG GAT TTG GTC AAG GAG CTT GAC AGA GAC        630
Gly Thr Gln Gly Lys Ile Val Asp Leu Val Lys Glu Leu Asp Arg Asp
185                 190                 195

ACA GTT TTT GCT CTG GTG AAT TAC ATC TTC TTT AAA GGC AAA TGG GAG        678
Thr Val Phe Ala Leu Val Asn Tyr Ile Phe Phe Lys Gly Lys Trp Glu
200                 205                 210                 215

AGA CCC TTT GAA GTC AAG GAC ACC GAG GAA GAG GAC TTC CAC GTG GAC        726
Arg Pro Phe Glu Val Lys Asp Thr Glu Glu Glu Asp Phe His Val Asp
                220                 225                 230

CAG GTG ACC ACC GTG AAG GTG CCT ATG ATG AAG CGT TTA GGC ATG TTT        774
Gln Val Thr Thr Val Lys Val Pro Met Met Lys Arg Leu Gly Met Phe
            235                 240                 245

AAC ATC CAG CAC TGT AAG AAG CTG TCC AGC TGG GTG CTG CTG ATG AAA        822
Asn Ile Gln His Cys Lys Lys Leu Ser Ser Trp Val Leu Leu Met Lys
        250                 255                 260

TAC CTG GGC AAT GCC ACC GCC ATG TTC TTC CTG CCT GAT GAG GGG AAA        870
Tyr Leu Gly Asn Ala Thr Ala Met Phe Phe Leu Pro Asp Glu Gly Lys
265                 270                 275

CTA CAG CAC CTG GAA AAT GAA CTC ACC CAC GAT ATC ATC ACC AAG TTC        918
Leu Gln His Leu Glu Asn Glu Leu Thr His Asp Ile Ile Thr Lys Phe
280                 285                 290                 295

CTG GAA AAT GAA GAC AGA AGG TCT GCC AGC TTA CAT TTA CCC AAA CTG        966
Leu Glu Asn Glu Asp Arg Arg Ser Ala Ser Leu His Leu Pro Lys Leu
                300                 305                 310
```

```
TCC ATT ACT GGA ACC TAT GAT CTG AAG AGC GTC CTG GGT CAA CTG GGC         1014
Ser Ile Thr Gly Thr Tyr Asp Leu Lys Ser Val Leu Gly Gln Leu Gly
        315             320                 325

ATC ACT AAG GTC TTC AGC AAT GGG GCT GAC CTC TCC GGG GTC ACA GAG         1062
Ile Thr Lys Val Phe Ser Asn Gly Ala Asp Leu Ser Gly Val Thr Glu
        330             335                 340

GAG GCA CCC CTG AAG CTC TCC AAG GCC GTG CAT AAG GCT GTG CTG ACC         1110
Glu Ala Pro Leu Lys Leu Ser Lys Ala Val His Lys Ala Val Leu Thr
        345             350                 355

ATC GAC GAG AAA GGG ACT GAA GCT GCT GGG GCC ATG TTT TTA GAG GCC         1158
Ile Asp Glu Lys Gly Thr Glu Ala Ala Gly Ala Met Phe Leu Glu Ala
        360             365                 370             375

ATA CCC ATG TCT ATC CCC CCC GAG GTC AAG TTC AAC AAA CCC TTT GTC         1206
Ile Pro Met Ser Ile Pro Pro Glu Val Lys Phe Asn Lys Pro Phe Val
                380             385                 390

TTC TTA ATG ATT GAA CAA AAT ACC AAG TCT CCC CTC TTC ATG GGA AAA         1254
Phe Leu Met Ile Glu Gln Asn Thr Lys Ser Pro Leu Phe Met Gly Lys
                395             400                 405

GTG GTG AAT CCC ACC CAA AAA TAACTGCTCG CTCCTCAACC CCTCCCCTCC            1305
Val Val Asn Pro Thr Gln Lys
        410             415

ATCCCTGGCC CCCTCCCTGG ATGACATTAA AGAAGGGTTG AGCTGGAAAA A                1356
```

( 2 ) INFORMATION FOR SEQ ID NO:17:

( i ) SEQUENCE CHARACTERISTICS:
        ( A ) LENGTH: 414 amino acids
        ( B ) TYPE: amino acid
        ( D ) TOPOLOGY: linear ( i i ) MOLECULE TYPE: protein ( x i ) SEQUENCE DESCRIPTION: SEQ ID NO:17:

```
Met Pro Ser Ser Val Ser Trp Gly Ile Leu Leu Leu Ala Gly Leu Cys
 1               5                  10                  15

Cys Leu Val Pro Val Ser Leu Ala Glu Asp Pro Gln Gly Asp Ala Ala
                20                  25                  30

Gln Lys Thr Asp Thr Ser His His Asp Gln Asp His Pro Thr Phe Asn
            35                  40                  45

Lys Ile Thr Pro Asn Leu Ala Glu Phe Ala Phe Ser Leu Tyr Arg Gln
        50                  55                  60

Leu Ala His Gln Ser Asn Ser Thr Asn Ile Phe Phe Ser Pro Val Ser
65                  70                  75                  80

Ile Ala Thr Ala Phe Ala Met Leu Ser Leu Gly Thr Lys Ala Asp Thr
                85                  90                  95

His Asp Glu Ile Leu Glu Gly Leu Asn Phe Asn Leu Thr Glu Ile Pro
            100                 105                 110

Glu Pro Gln Ile His Glu Gly Phe Gln Glu Leu Leu Arg Thr Leu Asn
        115                 120                 125

Gln Leu Gln Leu Thr Thr Gly Asn Gly Leu Phe Leu Ser Glu Gly Leu
    130                 135                 140

Lys Leu Val Asp Lys Phe Leu Glu Asp Val Lys Lys Leu Tyr His Ser
145                 150                 155                 160

Glu Ala Phe Thr Val Asn Phe Gly Asp Thr Glu Glu Ala Lys Lys Gln
                165                 170                 175

Ile Asn Asp Tyr Val Glu Lys Gly Thr Gln Gly Lys Ile Val Asp Leu
            180                 185                 190
```

| Val | Lys | Glu | Leu | Asp | Arg | Asp | Thr | Val | Phe | Ala | Leu | Val | Asn | Tyr | Ile |
|     | 195 |     |     |     |     | 200 |     |     |     |     | 205 |     |     |     |     |

| Phe | Phe | Lys | Gly | Lys | Trp | Glu | Arg | Pro | Phe | Glu | Val | Lys | Asp | Thr | Glu |
|     | 210 |     |     |     | 215 |     |     |     |     | 220 |     |     |     |     |     |

| Glu | Glu | Asp | Phe | His | Val | Asp | Gln | Val | Thr | Thr | Val | Lys | Val | Pro | Met |
| 225 |     |     |     |     | 230 |     |     |     |     | 235 |     |     |     |     | 240 |

| Met | Lys | Arg | Leu | Gly | Met | Phe | Asn | Ile | Gln | His | Cys | Lys | Lys | Leu | Ser |
|     |     |     |     | 245 |     |     |     |     | 250 |     |     |     |     | 255 |     |

| Ser | Trp | Val | Leu | Leu | Met | Lys | Tyr | Leu | Gly | Asn | Ala | Thr | Ala | Met | Phe |
|     |     |     | 260 |     |     |     |     | 265 |     |     |     |     | 270 |     |     |

| Phe | Leu | Pro | Asp | Glu | Gly | Lys | Leu | Gln | His | Leu | Glu | Asn | Glu | Leu | Thr |
|     |     | 275 |     |     |     |     | 280 |     |     |     |     | 285 |     |     |     |

| His | Asp | Ile | Ile | Thr | Lys | Phe | Leu | Glu | Asn | Glu | Asp | Arg | Arg | Ser | Ala |
|     | 290 |     |     |     |     |     | 295 |     |     |     | 300 |     |     |     |     |

| Ser | Leu | His | Leu | Pro | Lys | Leu | Ser | Ile | Thr | Gly | Thr | Tyr | Asp | Leu | Lys |
| 305 |     |     |     |     | 310 |     |     |     |     | 315 |     |     |     |     | 320 |

| Ser | Val | Leu | Gly | Gln | Leu | Gly | Ile | Thr | Lys | Val | Phe | Ser | Asn | Gly | Ala |
|     |     |     |     | 325 |     |     |     |     | 330 |     |     |     |     | 335 |     |

| Asp | Leu | Ser | Gly | Val | Thr | Glu | Glu | Ala | Pro | Leu | Lys | Leu | Ser | Lys | Ala |
|     |     |     | 340 |     |     |     |     | 345 |     |     |     |     | 350 |     |     |

| Val | His | Lys | Ala | Val | Leu | Thr | Ile | Asp | Glu | Lys | Gly | Thr | Glu | Ala | Ala |
|     |     | 355 |     |     |     |     | 360 |     |     |     |     | 365 |     |     |     |

| Gly | Ala | Met | Phe | Leu | Glu | Ala | Ile | Pro | Met | Ser | Ile | Pro | Pro | Glu | Val |
|     | 370 |     |     |     |     | 375 |     |     |     |     | 380 |     |     |     |     |

| Lys | Phe | Asn | Lys | Pro | Phe | Val | Phe | Leu | Met | Ile | Glu | Gln | Asn | Thr | Lys |
| 385 |     |     |     |     | 390 |     |     |     |     | 395 |     |     |     |     | 400 |

| Ser | Pro | Leu | Phe | Met | Gly | Lys | Val | Val | Asn | Pro | Thr | Gln | Lys |
|     |     |     |     | 405 |     |     |     |     | 410 |     |     |     |     |

( 2 ) INFORMATION FOR SEQ ID NO:18:

( i ) SEQUENCE CHARACTERISTICS:
        ( A ) LENGTH: 1356 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 34..1278
        ( D ) OTHER INFORMATION: /product="alpha-1-antitrypsin
                Portland variant"
        / standard_name="alpha-1-antitrypsin Portland"

( x i ) SEQUENCE DESCRIPTION: SEQ ID NO:18:

| GCACCACCAC | TGACCTGGGA | CAGTGAATCG | ACA | ATG | CCG | TCT | TCT | GTC | TCG | TGG | 54 |
|            |            |            |     | Met | Pro | Ser | Ser | Val | Ser | Trp |    |
|            |            |            |     | 1   |     |     |     | 5   |     |     |    |

| GGC | ATC | CTC | CTG | CTG | GCA | GGC | CTG | TGC | TGC | CTG | GTC | CCT | GTC | TCC | CTG | 102 |
| Gly | Ile | Leu | Leu | Leu | Ala | Gly | Leu | Cys | Cys | Leu | Val | Pro | Val | Ser | Leu |     |
|     |     | 10  |     |     |     |     | 15  |     |     |     |     | 20  |     |     |     |     |

| GCT | GAG | GAT | CCC | CAG | GGA | GAT | GCT | GCC | CAG | AAG | ACA | GAT | ACA | TCC | CAC | 150 |
| Ala | Glu | Asp | Pro | Gln | Gly | Asp | Ala | Ala | Gln | Lys | Thr | Asp | Thr | Ser | His |     |
|     | 25  |     |     |     |     | 30  |     |     |     |     | 35  |     |     |     |     |     |

| CAT | GAT | CAG | GAT | CAC | CCA | ACC | TTC | AAC | AAG | ATC | ACC | CCC | AAC | CTG | GCT | 198 |
| His | Asp | Gln | Asp | His | Pro | Thr | Phe | Asn | Lys | Ile | Thr | Pro | Asn | Leu | Ala |     |
| 40  |     |     |     |     | 45  |     |     |     |     | 50  |     |     |     |     | 55  |     |

| | | | | | | | | | | | | | | | | |
|---|---|---|---|---|---|---|---|---|---|---|---|---|---|---|---|---|
| GAG | TTC | GCC | TTC | AGC | CTA | TAC | CGC | CAG | CTG | GCA | CAC | CAG | TCC | AAC | AGC | 246 |
| Glu | Phe | Ala | Phe | Ser | Leu | Tyr | Arg | Gln | Leu | Ala | His | Gln | Ser | Asn | Ser | |
| | | | | 60 | | | | 65 | | | | | | 70 | | |
| ACC | AAT | ATC | TTC | TTC | TCC | CCA | GTG | AGC | ATC | GCT | ACA | GCC | TTT | GCA | ATG | 294 |
| Thr | Asn | Ile | Phe | Phe | Ser | Pro | Val | Ser | Ile | Ala | Thr | Ala | Phe | Ala | Met | |
| | | | 75 | | | | | 80 | | | | | 85 | | | |
| CTC | TCC | CTG | GGG | ACC | AAG | GCT | GAC | ACT | CAC | GAT | GAA | ATC | CTG | GAG | GGC | 342 |
| Leu | Ser | Leu | Gly | Thr | Lys | Ala | Asp | Thr | His | Asp | Glu | Ile | Leu | Glu | Gly | |
| | | 90 | | | | | 95 | | | | | 100 | | | | |
| CTG | AAT | TTC | AAC | CTC | ACG | GAG | ATT | CCG | GAG | CCT | CAG | ATC | CAT | GAA | GGC | 390 |
| Leu | Asn | Phe | Asn | Leu | Thr | Glu | Ile | Pro | Glu | Pro | Gln | Ile | His | Glu | Gly | |
| | 105 | | | | | 110 | | | | | 115 | | | | | |
| TTC | CAG | GAA | CTC | CTC | CGT | ACC | CTC | AAC | CAG | CTC | CAG | CTG | ACC | ACC | GGC | 438 |
| Phe | Gln | Glu | Leu | Leu | Arg | Thr | Leu | Asn | Gln | Leu | Gln | Leu | Thr | Thr | Gly | |
| 120 | | | | | 125 | | | | | 130 | | | | | 135 | |
| AAT | GGC | CTG | TTC | CTC | AGC | GAG | GGC | CTG | AAG | CTA | GTG | GAT | AAG | TTT | TTG | 486 |
| Asn | Gly | Leu | Phe | Leu | Ser | Glu | Gly | Leu | Lys | Leu | Val | Asp | Lys | Phe | Leu | |
| | | | | 140 | | | | | 145 | | | | | 150 | | |
| GAG | GAT | GTT | AAA | AAG | TTG | TAC | CAC | TCA | GAA | GCC | TTC | ACT | GTC | AAC | TTC | 534 |
| Glu | Asp | Val | Lys | Lys | Leu | Tyr | His | Ser | Glu | Ala | Phe | Thr | Val | Asn | Phe | |
| | | | 155 | | | | | 160 | | | | | 165 | | | |
| GGG | GAC | ACC | GAA | GAG | GCC | AAG | AAA | CAG | ATC | AAC | GAT | TAC | GTG | GAG | AAG | 582 |
| Gly | Asp | Thr | Glu | Glu | Ala | Lys | Lys | Gln | Ile | Asn | Asp | Tyr | Val | Glu | Lys | |
| | | 170 | | | | | 175 | | | | | 180 | | | | |
| GGT | ACT | CAA | GGG | AAA | ATT | GTG | GAT | TTG | GTC | AAG | GAG | CTT | GAC | AGA | GAC | 630 |
| Gly | Thr | Gln | Gly | Lys | Ile | Val | Asp | Leu | Val | Lys | Glu | Leu | Asp | Arg | Asp | |
| | 185 | | | | | 190 | | | | | 195 | | | | | |
| ACA | GTT | TTT | GCT | CTG | GTG | AAT | TAC | ATC | TTC | TTT | AAA | GGC | AAA | TGG | GAG | 678 |
| Thr | Val | Phe | Ala | Leu | Val | Asn | Tyr | Ile | Phe | Phe | Lys | Gly | Lys | Trp | Glu | |
| 200 | | | | | 205 | | | | | 210 | | | | | 215 | |
| AGA | CCC | TTT | GAA | GTC | AAG | GAC | ACC | GAG | GAA | GAG | GAC | TTC | CAC | GTG | GAC | 726 |
| Arg | Pro | Phe | Glu | Val | Lys | Asp | Thr | Glu | Glu | Glu | Asp | Phe | His | Val | Asp | |
| | | | | 220 | | | | | 225 | | | | | 230 | | |
| CAG | GTG | ACC | ACC | GTG | AAG | GTG | CCT | ATG | ATG | AAG | CGT | TTA | GGC | ATG | TTT | 774 |
| Gln | Val | Thr | Thr | Val | Lys | Val | Pro | Met | Met | Lys | Arg | Leu | Gly | Met | Phe | |
| | | | 235 | | | | | 240 | | | | | 245 | | | |
| AAC | ATC | CAG | CAC | TGT | AAG | AAG | CTG | TCC | AGC | TGG | GTG | CTG | CTG | ATG | AAA | 822 |
| Asn | Ile | Gln | His | Cys | Lys | Lys | Leu | Ser | Ser | Trp | Val | Leu | Leu | Met | Lys | |
| | | 250 | | | | | 255 | | | | | 260 | | | | |
| TAC | CTG | GGC | AAT | GCC | ACC | GCC | ATG | TTC | TTC | CTG | CCT | GAT | GAG | GGG | AAA | 870 |
| Tyr | Leu | Gly | Asn | Ala | Thr | Ala | Met | Phe | Phe | Leu | Pro | Asp | Glu | Gly | Lys | |
| | 265 | | | | | 270 | | | | | 275 | | | | | |
| CTA | CAG | CAC | CTG | GAA | AAT | GAA | CTC | ACC | CAC | GAT | ATC | ATC | ACC | AAG | TTC | 918 |
| Leu | Gln | His | Leu | Glu | Asn | Glu | Leu | Thr | His | Asp | Ile | Ile | Thr | Lys | Phe | |
| 280 | | | | | 285 | | | | | 290 | | | | | 295 | |
| CTG | GAA | AAT | GAA | GAC | AGA | AGG | TCT | GCC | AGC | TTA | CAT | TTA | CCC | AAA | CTG | 966 |
| Leu | Glu | Asn | Glu | Asp | Arg | Arg | Ser | Ala | Ser | Leu | His | Leu | Pro | Lys | Leu | |
| | | | | 300 | | | | | 305 | | | | | 310 | | |
| TCC | ATT | ACT | GGA | ACC | TAT | GAT | CTG | AAG | AGC | GTC | CTG | GGT | CAA | CTG | GGC | 1014 |
| Ser | Ile | Thr | Gly | Thr | Tyr | Asp | Leu | Lys | Ser | Val | Leu | Gly | Gln | Leu | Gly | |
| | | | 315 | | | | | 320 | | | | | 325 | | | |
| ATC | ACT | AAG | GTC | TTC | AGC | AAT | GGG | GCT | GAC | CTC | TCC | GGG | GTC | ACA | GAG | 1062 |
| Ile | Thr | Lys | Val | Phe | Ser | Asn | Gly | Ala | Asp | Leu | Ser | Gly | Val | Thr | Glu | |
| | | 330 | | | | | 335 | | | | | 340 | | | | |
| GAG | GCA | CCC | CTG | AAG | CTC | TCC | AAG | GCC | GTG | CAT | AAG | GCT | GTG | CTG | ACC | 1110 |
| Glu | Ala | Pro | Leu | Lys | Leu | Ser | Lys | Ala | Val | His | Lys | Ala | Val | Leu | Thr | |
| | 345 | | | | | 350 | | | | | 355 | | | | | |
| ATC | GAC | GAG | AAA | GGG | ACT | GAA | GCT | GCT | GGG | GCC | ATG | TTT | TTA | GAG | CGC | 1158 |
| Ile | Asp | Glu | Lys | Gly | Thr | Glu | Ala | Ala | Gly | Ala | Met | Phe | Leu | Glu | Arg | |
| 360 | | | | | 365 | | | | | 370 | | | | | 375 | |

| ATA | CCC | AGG | TCT | ATC | CCC | CCC | GAG | GTC | AAG | TTC | AAC | AAA | CCC | TTT | GTC | 1206 |
|-----|-----|-----|-----|-----|-----|-----|-----|-----|-----|-----|-----|-----|-----|-----|-----|------|
| Ile | Pro | Arg | Ser | Ile | Pro | Pro | Glu | Val | Lys | Phe | Asn | Lys | Pro | Phe | Val | |
| | | | 380 | | | | | 385 | | | | | 390 | | | |

| TTC | TTA | ATG | ATT | GAA | CAA | AAT | ACC | AAG | TCT | CCC | CTC | TTC | ATG | GGA | AAA | 1254 |
|-----|-----|-----|-----|-----|-----|-----|-----|-----|-----|-----|-----|-----|-----|-----|-----|------|
| Phe | Leu | Met | Ile | Glu | Gln | Asn | Thr | Lys | Ser | Pro | Leu | Phe | Met | Gly | Lys | |
| | | | 395 | | | | 400 | | | | | 405 | | | | |

| GTG | GTG | AAT | CCC | ACC | CAA | AAA | TAACTGCTCG | CTCCTCAACC | CCTCCCTCC | 1305 |
|-----|-----|-----|-----|-----|-----|-----|-----|-----|-----|------|
| Val | Val | Asn | Pro | Thr | Gln | Lys | | | | |
| | | 410 | | | | 415 | | | | |

ATCCCTGGCC CCCTCCCTGG ATGACATTAA AGAAGGGTTG AGCTGGAAAA A    1356

( 2 ) INFORMATION FOR SEQ ID NO:19:

( i ) SEQUENCE CHARACTERISTICS:
        ( A ) LENGTH: 414 amino acids
        ( B ) TYPE: amino acid
        ( D ) TOPOLOGY: linear ( i i ) MOLECULE TYPE: protein ( x i ) SEQUENCE DESCRIPTION: SEQ ID NO:19:

| Met | Pro | Ser | Ser | Val | Ser | Trp | Gly | Ile | Leu | Leu | Ala | Gly | Leu | Cys |
|-----|-----|-----|-----|-----|-----|-----|-----|-----|-----|-----|-----|-----|-----|-----|
| 1 | | | | 5 | | | | | 10 | | | | | 15 |

| Cys | Leu | Val | Pro | Val | Ser | Leu | Ala | Glu | Asp | Pro | Gln | Gly | Asp | Ala | Ala |
|-----|-----|-----|-----|-----|-----|-----|-----|-----|-----|-----|-----|-----|-----|-----|-----|
| | | | 20 | | | | | 25 | | | | | 30 | | |

| Gln | Lys | Thr | Asp | Thr | Ser | His | His | Asp | Gln | Asp | His | Pro | Thr | Phe | Asn |
|-----|-----|-----|-----|-----|-----|-----|-----|-----|-----|-----|-----|-----|-----|-----|-----|
| | | 35 | | | | | 40 | | | | | 45 | | | |

| Lys | Ile | Thr | Pro | Asn | Leu | Ala | Glu | Phe | Ala | Phe | Ser | Leu | Tyr | Arg | Gln |
|-----|-----|-----|-----|-----|-----|-----|-----|-----|-----|-----|-----|-----|-----|-----|-----|
| | 50 | | | | | 55 | | | | | 60 | | | | |

| Leu | Ala | His | Gln | Ser | Asn | Ser | Thr | Asn | Ile | Phe | Phe | Ser | Pro | Val | Ser |
|-----|-----|-----|-----|-----|-----|-----|-----|-----|-----|-----|-----|-----|-----|-----|-----|
| 65 | | | | | 70 | | | | | 75 | | | | | 80 |

| Ile | Ala | Thr | Ala | Phe | Ala | Met | Leu | Ser | Leu | Gly | Thr | Lys | Ala | Asp | Thr |
|-----|-----|-----|-----|-----|-----|-----|-----|-----|-----|-----|-----|-----|-----|-----|-----|
| | | | | 85 | | | | | 90 | | | | | 95 | |

| His | Asp | Glu | Ile | Leu | Glu | Gly | Leu | Asn | Phe | Asn | Leu | Thr | Glu | Ile | Pro |
|-----|-----|-----|-----|-----|-----|-----|-----|-----|-----|-----|-----|-----|-----|-----|-----|
| | | | | 100 | | | | | 105 | | | | | 110 | |

| Glu | Pro | Gln | Ile | His | Glu | Gly | Phe | Gln | Glu | Leu | Leu | Arg | Thr | Leu | Asn |
|-----|-----|-----|-----|-----|-----|-----|-----|-----|-----|-----|-----|-----|-----|-----|-----|
| | | | 115 | | | | | 120 | | | | | 125 | | |

| Gln | Leu | Gln | Leu | Thr | Thr | Gly | Asn | Gly | Leu | Phe | Leu | Ser | Glu | Gly | Leu |
|-----|-----|-----|-----|-----|-----|-----|-----|-----|-----|-----|-----|-----|-----|-----|-----|
| | 130 | | | | | 135 | | | | | 140 | | | | |

| Lys | Leu | Val | Asp | Lys | Phe | Leu | Glu | Asp | Val | Lys | Lys | Leu | Tyr | His | Ser |
|-----|-----|-----|-----|-----|-----|-----|-----|-----|-----|-----|-----|-----|-----|-----|-----|
| 145 | | | | | 150 | | | | | 155 | | | | | 160 |

| Glu | Ala | Phe | Thr | Val | Asn | Phe | Gly | Asp | Thr | Glu | Glu | Ala | Lys | Lys | Gln |
|-----|-----|-----|-----|-----|-----|-----|-----|-----|-----|-----|-----|-----|-----|-----|-----|
| | | | | 165 | | | | | 170 | | | | | 175 | |

| Ile | Asn | Asp | Tyr | Val | Glu | Lys | Gly | Thr | Gln | Gly | Lys | Ile | Val | Asp | Leu |
|-----|-----|-----|-----|-----|-----|-----|-----|-----|-----|-----|-----|-----|-----|-----|-----|
| | | | 180 | | | | | 185 | | | | | 190 | | |

| Val | Lys | Glu | Leu | Asp | Arg | Asp | Thr | Val | Phe | Ala | Leu | Val | Asn | Tyr | Ile |
|-----|-----|-----|-----|-----|-----|-----|-----|-----|-----|-----|-----|-----|-----|-----|-----|
| | | 195 | | | | | 200 | | | | | 205 | | | |

| Phe | Phe | Lys | Gly | Lys | Trp | Glu | Arg | Pro | Phe | Glu | Val | Lys | Asp | Thr | Glu |
|-----|-----|-----|-----|-----|-----|-----|-----|-----|-----|-----|-----|-----|-----|-----|-----|
| | 210 | | | | | 215 | | | | | 220 | | | | |

| Glu | Glu | Asp | Phe | His | Val | Asp | Gln | Val | Thr | Thr | Val | Lys | Val | Pro | Met |
|-----|-----|-----|-----|-----|-----|-----|-----|-----|-----|-----|-----|-----|-----|-----|-----|
| 225 | | | | | 230 | | | | | 235 | | | | | 240 |

| Met | Lys | Arg | Leu | Gly | Met | Phe | Asn | Ile | Gln | His | Cys | Lys | Lys | Leu | Ser |
|-----|-----|-----|-----|-----|-----|-----|-----|-----|-----|-----|-----|-----|-----|-----|-----|
| | | | | 245 | | | | | 250 | | | | | 255 | |

| Ser | Trp | Val | Leu | Leu | Met | Lys | Tyr | Leu | Gly | Asn | Ala | Thr | Ala | Met | Phe |
|-----|-----|-----|-----|-----|-----|-----|-----|-----|-----|-----|-----|-----|-----|-----|-----|
| | | | 260 | | | | | 265 | | | | | 270 | | |

| Phe | Leu | Pro | Asp | Glu | Gly | Lys | Leu | Gln | His | Leu | Glu | Asn | Glu | Leu | Thr |
|-----|-----|-----|-----|-----|-----|-----|-----|-----|-----|-----|-----|-----|-----|-----|-----|
| | | 275 | | | | | 280 | | | | | 285 | | | |

| His | Asp | Ile | Ile | Thr | Lys | Phe | Leu | Glu | Asn | Glu | Asp | Arg | Arg | Ser | Ala |
| | 290 | | | | 295 | | | | | 300 | | | | | |
| Ser | Leu | His | Leu | Pro | Lys | Leu | Ser | Ile | Thr | Gly | Thr | Tyr | Asp | Leu | Lys |
| 305 | | | | | 310 | | | | | 315 | | | | | 320 |
| Ser | Val | Leu | Gly | Gln | Leu | Gly | Ile | Thr | Lys | Val | Phe | Ser | Asn | Gly | Ala |
| | | | | 325 | | | | | 330 | | | | | 335 | |
| Asp | Leu | Ser | Gly | Val | Thr | Glu | Glu | Ala | Pro | Leu | Lys | Leu | Ser | Lys | Ala |
| | | | 340 | | | | | 345 | | | | | 350 | | |
| Val | His | Lys | Ala | Val | Leu | Thr | Ile | Asp | Glu | Lys | Gly | Thr | Glu | Ala | Ala |
| | | 355 | | | | | 360 | | | | | 365 | | | |
| Gly | Ala | Met | Phe | Leu | Glu | Arg | Ile | Pro | Arg | Ser | Ile | Pro | Pro | Glu | Val |
| | 370 | | | | | 375 | | | | | 380 | | | | |
| Lys | Phe | Asn | Lys | Pro | Phe | Val | Phe | Leu | Met | Ile | Glu | Gln | Asn | Thr | Lys |
| 385 | | | | | 390 | | | | | 395 | | | | | 400 |
| Ser | Pro | Leu | Phe | Met | Gly | Lys | Val | Val | Asn | Pro | Thr | Gln | Lys | | |
| | | | | 405 | | | | | 410 | | | | | | |

( 2 ) INFORMATION FOR SEQ ID NO:20:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1..4
        ( D ) OTHER INFORMATION: /label=Modified-sites
            / note="The amino terminus is derivatized by a
            butoxycarbonyl group, and the carboxyl terminus is
            derivatized by a 4-methylcoumaryl-7-amide group;"

( x i ) SEQUENCE DESCRIPTION: SEQ ID NO:20:

Arg  Val  Arg  Arg
    1

( 2 ) INFORMATION FOR SEQ ID NO:21:

( i ) SEQUENCE CHARACTERISTICS:
        ( A ) LENGTH: 4 amino acids
        ( B ) TYPE: amino acid
        ( D ) TOPOLOGY: linear ( i i ) MOLECULE TYPE: peptide ( i x ) FEATURE:
        ( A ) NAME/KEY: Modified-site
        ( B ) LOCATION: 1..4
        ( D ) OTHER INFORMATION: /label=Modified-sites
            / note="The amino terminus is derivatized by a
            butoxycarbonyl group, and the carboxyl terminus is
            derivatized by a para-nitroanilide group; "

( x i ) SEQUENCE DESCRIPTION: SEQ ID NO:21:

Ala  Ala  Pro  Ala
    1